US011013875B2

(12) United States Patent
Tang et al.

(10) Patent No.: US 11,013,875 B2
(45) Date of Patent: May 25, 2021

(54) LOW COST CPAP FLOW GENERATOR AND HUMIDIFIER ASSEMBLY

(71) Applicant: ResMed Pty Ltd, Bella Vista (AU)

(72) Inventors: Zhuo Ran Tang, Maroubra (AU); Cem Tarakci, Bella Vista (AU); John Michael Snow, Killarney Heights (AU); Kenneth Lee, Lindfield (AU); Steven Paul Farrugia, Lugarno (AU); Dmitri Anatolievich Doudkine, Chatswood (AU); Ian Malcolm Smith, Westleigh (AU)

(73) Assignee: ResMed Pty Ltd, Bella Vista (AU)

( * ) Notice: Subject to any disclaimer, the term of this patent is extended or adjusted under 35 U.S.C. 154(b) by 148 days.

(21) Appl. No.: 16/044,422

(22) Filed: Jul. 24, 2018

(65) Prior Publication Data
US 2018/0326167 A1 Nov. 15, 2018

Related U.S. Application Data

(62) Division of application No. 13/890,302, filed on May 9, 2013, now Pat. No. 10,058,665, which is a division
(Continued)

(51) Int. Cl.
*A61M 16/00* (2006.01)
*A61M 16/10* (2006.01)
(Continued)

(52) U.S. Cl.
CPC .... *A61M 16/0057* (2013.01); *A61M 16/0051* (2013.01); *A61M 16/0069* (2014.02);
(Continued)

(58) Field of Classification Search
CPC .......... A61M 16/0057; A61M 16/0051; A61M 16/0069; A61M 16/024; A61M 16/109;
(Continued)

(56) References Cited

U.S. PATENT DOCUMENTS

| 1,085,833 A | 2/1914 | Wilson |
| 2,840,682 A | 6/1958 | Rubenstein et al. |
| (Continued) | | |

FOREIGN PATENT DOCUMENTS

| AU | 14863/95 | 9/1995 |
| CN | 101306218 | 11/2008 |
| (Continued) | | |

OTHER PUBLICATIONS

Notice of Reasons for Rejection dated Aug. 7, 2017 issued in Japanese Application No. 2016-175411 with English translation (13 pages).
(Continued)

*Primary Examiner* — Steven O Douglas
(74) *Attorney, Agent, or Firm* — Nixon & Vanderhye P.C.

(57) ABSTRACT

A method for controlling a humidifier of a CPAP device including a controller, the method including controlling a heating element in the humidifier with command signals from the controller, sensing a temperature of a fluid in the humidifier with a sensor in the humidifier that transmits signals to the controller, establishing an acceptable operating range for the signal transmitted to the controller; determining whether the transmitted signal is within the acceptable operating range, if the signal is within the acceptable operating range treating the signal as being indicative of the temperature of the fluid in the humidifier and using the signal to control the heating element, and if the signal is outside of the acceptable operating range, the controller determines the humidifier to be unavailable.

20 Claims, 21 Drawing Sheets

Related U.S. Application Data of application No. 11/988,934, filed as application No. PCT/AU2006/001173 on Aug. 15, 2006, now Pat. No. 8,739,780.

(60) Provisional application No. 60/707,951, filed on Aug. 15, 2005.

(51) Int. Cl.
*A61M 16/14* (2006.01)
*A61M 16/16* (2006.01)

(52) U.S. Cl.
CPC ........ *A61M 16/024* (2017.08); *A61M 16/109* (2014.02); *A61M 16/1075* (2013.01); *A61M 16/142* (2014.02); *A61M 16/16* (2013.01); *A61M 2205/3368* (2013.01); *A61M 2205/3561* (2013.01); *A61M 2205/3584* (2013.01)

(58) Field of Classification Search
CPC ............ A61M 16/1075; A61M 16/142; A61M 16/16; A61M 2205/3368; A61M 2205/3561; A61M 2205/3584
See application file for complete search history.

(56) References Cited

U.S. PATENT DOCUMENTS

| | | |
|---|---|---|
| 2,875,314 A | 2/1959 | Schreyer |
| 3,584,192 A | 6/1971 | Maag |
| 3,659,604 A | 5/1972 | Melville et al. |
| 3,871,373 A | 3/1975 | Jackson |
| 3,982,095 A | 9/1976 | Robinson |
| 3,987,133 A | 10/1976 | Andra |
| 4,014,382 A | 3/1977 | Heath |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,086,305 A | 4/1978 | Dobritz |
| 4,110,419 A | 8/1978 | Miller |
| 4,146,597 A | 3/1979 | Eckstein et al. |
| 4,152,379 A | 5/1979 | Suhr |
| 4,155,961 A | 5/1979 | Benthin |
| 4,201,204 A | 5/1980 | Rinne et al. |
| 4,203,027 A | 5/1980 | O'Hare et al. |
| 4,367,734 A | 1/1983 | Benthin |
| 4,430,994 A | 2/1984 | Clawson et al. |
| 4,561,287 A | 2/1985 | Rowland |
| 4,532,088 A | 7/1985 | Miller |
| 4,621,632 A | 11/1986 | Bartels |
| 4,657,713 A | 4/1987 | Miller |
| 4,686,354 A | 8/1987 | Makin |
| 4,708,831 A | 11/1987 | Elsworth et al. |
| 4,753,758 A | 6/1988 | Miller |
| 4,829,998 A | 5/1989 | Jackson |
| 4,861,523 A | 8/1989 | Beran |
| 4,865,777 A | 9/1989 | Weiler et al. |
| 4,891,171 A | 1/1990 | Weiler et al. |
| 4,910,384 A | 3/1990 | Silver |
| 4,911,357 A | 3/1990 | Kitamura |
| 4,913,140 A | 4/1990 | Orec et al. |
| 4,921,642 A | 5/1990 | LaTorraca |
| 5,031,612 A | 7/1991 | Clementi |
| 5,062,145 A | 10/1991 | Zwaan et al. |
| 5,092,326 A | 3/1992 | Winn et al. |
| 5,163,423 A | 11/1992 | Suzuki |
| 5,230,331 A | 7/1993 | Rusz et al. |
| 5,231,979 A | 8/1993 | Rose et al. |
| 5,357,948 A | 10/1994 | Eilentropp |
| 5,367,604 A | 11/1994 | Murray |
| 5,368,786 A | 11/1994 | Dinauer et al. |
| 5,392,770 A | 2/1995 | Clawson et al. |
| 5,411,052 A | 5/1995 | Murray |
| 5,429,123 A | 7/1995 | Shaffer et al. |
| 5,445,143 A | 8/1995 | Sims |
| 5,454,061 A | 9/1995 | Carlson |
| 5,468,961 A | 11/1995 | Gradon et al. |
| 5,529,060 A | 6/1996 | Salmon et al. |
| 5,537,996 A | 7/1996 | McPhee |
| 5,537,997 A | 7/1996 | Mechlenburg et al. |
| 5,558,084 A | 9/1996 | Daniell et al. |
| 5,564,415 A | 10/1996 | Dobson et al. |
| 5,588,423 A | 12/1996 | Smith |
| 5,598,837 A | 2/1997 | Sirianne, Jr. et al. |
| 5,640,951 A | 6/1997 | Huddart et al. |
| 5,655,522 A | 8/1997 | Mechlenburg et al. |
| 5,673,687 A | 10/1997 | Dobson et al. |
| 5,694,923 A | 12/1997 | Hete et al. |
| 5,740,795 A | 4/1998 | Brydon |
| 5,769,071 A | 6/1998 | Turnbull |
| 5,800,741 A | 9/1998 | Glenn et al. |
| 5,916,493 A | 6/1999 | Miller |
| 5,937,855 A | 8/1999 | Zdrojkowski et al. |
| 5,938,984 A | 8/1999 | Jung |
| 5,947,115 A | 9/1999 | Lordo et al. |
| 5,988,164 A | 11/1999 | Paluch |
| 6,010,118 A | 1/2000 | Milewicz |
| 6,017,315 A | 1/2000 | Starr et al. |
| 6,050,260 A | 4/2000 | Daniell et al. |
| 6,050,552 A | 4/2000 | Loescher et al. |
| 6,078,730 A | 6/2000 | Huddart et al. |
| 6,095,135 A | 8/2000 | Clawson et al. |
| 6,095,505 A | 8/2000 | Miller |
| 6,102,037 A | 8/2000 | Koch |
| 6,116,029 A | 9/2000 | Krawec |
| 6,135,432 A | 10/2000 | Hebblewhite et al. |
| 6,167,883 B1 | 1/2001 | Beran et al. |
| 6,201,223 B1 | 3/2001 | Nitta |
| 6,219,490 B1 | 4/2001 | Gibertoni et al. |
| 6,272,933 B1 | 8/2001 | Gradon et al. |
| 6,335,517 B1 | 1/2002 | Chauviaux et al. |
| 6,338,473 B1 | 1/2002 | Hebblewhite et al. |
| 6,349,722 B1 | 2/2002 | Gradon et al. |
| 6,349,724 B1 | 2/2002 | Burton et al. |
| 6,363,930 B1 | 4/2002 | Clawson et al. |
| 6,367,472 B1 | 4/2002 | Koch |
| 6,394,084 B1 | 5/2002 | Nitta |
| 6,398,197 B1 | 6/2002 | Dickinson et al. |
| 6,435,180 B1 | 8/2002 | Hewson et al. |
| 6,437,316 B1 | 8/2002 | Colman et al. |
| 6,470,885 B1 | 10/2002 | Blue et al. |
| 6,510,848 B1 | 1/2003 | Gibertoni |
| 6,520,021 B1 | 2/2003 | Wixey et al. |
| 6,523,810 B2 | 2/2003 | Offir et al. |
| 6,554,260 B1 | 4/2003 | Lipscombe et al. |
| 6,557,551 B2 | 5/2003 | Nitta |
| 6,584,972 B2 | 7/2003 | McPhee |
| 6,591,834 B1 | 7/2003 | Colla et al. |
| 6,592,107 B1 | 7/2003 | Wong |
| 6,598,604 B1 | 7/2003 | Seakins |
| 6,615,831 B1 | 9/2003 | Tuitt et al. |
| 6,629,934 B2 | 10/2003 | Mault et al. |
| 6,694,974 B1 | 2/2004 | George-Gradon et al. |
| 6,718,973 B2 | 4/2004 | Koch |
| 6,718,974 B1 | 4/2004 | Moberg |
| 6,745,768 B2 | 6/2004 | Colla et al. |
| 6,772,999 B2 | 8/2004 | Lipscombe et al. |
| 6,802,314 B2 | 10/2004 | McPhee |
| 6,827,340 B2 | 12/2004 | Austin et al. |
| 6,877,510 B2 | 4/2005 | Nitta |
| 6,895,803 B2 | 5/2005 | Seakins et al. |
| 6,918,389 B2 | 7/2005 | Seakins et al. |
| 6,935,337 B2 | 8/2005 | Virr et al. |
| 6,953,354 B2 | 10/2005 | Edirisuriya et al. |
| 7,040,317 B2 | 5/2006 | Colla et al. |
| 7,043,979 B2 | 5/2006 | Smith et al. |
| 7,073,500 B2 | 7/2006 | Kates |
| 7,079,758 B2 | 7/2006 | Sunaga et al. |
| 7,086,399 B2 | 8/2006 | Makinson et al. |
| 7,140,367 B2 | 11/2006 | White et al. |
| 7,146,979 B2 | 12/2006 | Seakins et al. |
| 7,291,240 B2 | 11/2007 | Smith et al. |
| 7,306,205 B2 | 12/2007 | Huddart et al. |

(56) References Cited

U.S. PATENT DOCUMENTS

| | | | |
|---|---|---|---|
| 7,413,173 | B2 | 8/2008 | DiMatteo et al. |
| 7,478,635 | B2 | 1/2009 | Wixey et al. |
| 7,516,740 | B2 | 4/2009 | Meier |
| 7,537,010 | B2 | 5/2009 | Colla et al. |
| 7,677,246 | B2 | 3/2010 | Kepler et al. |
| 8,006,691 | B2 | 8/2011 | Kenyon et al. |
| 8,069,854 | B2 | 12/2011 | Colla et al. |
| 8,485,182 | B2 | 7/2013 | Colla et al. |
| 8,720,439 | B1 | 5/2014 | Kolkowski |
| 8,910,631 | B2 | 12/2014 | Colla et al. |
| 9,802,022 | B2 | 10/2017 | Smith et al. |
| 2001/0050080 | A1 | 12/2001 | Pujol et al. |
| 2002/0078958 | A1 | 6/2002 | Stenzler |
| 2002/0112725 | A1 | 8/2002 | Thudor et al. |
| 2004/0055597 | A1 | 3/2004 | Virr et al. |
| 2004/0074493 | A1 | 4/2004 | Seakins et al. |
| 2004/0079370 | A1 | 4/2004 | Gradon et al. |
| 2004/0102731 | A1 | 5/2004 | Blackhurst et al. |
| 2004/0182386 | A1 | 9/2004 | Meier |
| 2004/0182392 | A1 | 9/2004 | Gerder et al. |
| 2004/0221844 | A1 | 11/2004 | Hunt et al. |
| 2006/0037613 | A1 | 2/2006 | Kwok et al. |
| 2006/0113690 | A1 | 6/2006 | Huddart et al. |
| 2006/0137445 | A1 | 6/2006 | Smith et al. |
| 2006/0191531 | A1 | 8/2006 | Mayer et al. |
| 2006/0213515 | A1 | 9/2006 | Bremner et al. |
| 2006/0231097 | A1* | 10/2006 | Dougherty .......... A61M 16/109 128/204.18 |
| 2006/0269440 | A1 | 11/2006 | Lee |
| 2006/0272639 | A1 | 12/2006 | Makinson et al. |
| 2006/0278221 | A1 | 12/2006 | Schermeier et al. |
| 2007/0051368 | A1 | 3/2007 | Seakins et al. |
| 2007/0079826 | A1 | 4/2007 | Kramer et al. |
| 2007/0125376 | A1 | 6/2007 | Reinstadtler |
| 2007/0169776 | A1 | 7/2007 | Kepler et al. |
| 2007/0230927 | A1 | 10/2007 | Kramer |
| 2007/0283957 | A1 | 12/2007 | Schobel et al. |
| 2007/0284361 | A1 | 12/2007 | Nadjafizadeh et al. |
| 2008/0028850 | A1 | 2/2008 | Payton et al. |
| 2008/0072900 | A1 | 3/2008 | Kenyon et al. |
| 2008/0105257 | A1 | 5/2008 | Klasek et al. |
| 2008/0302361 | A1 | 12/2008 | Snow et al. |
| 2008/0308100 | A1 | 12/2008 | Pujol et al. |
| 2009/0223514 | A1 | 9/2009 | Smith et al. |
| 2009/0229606 | A1 | 9/2009 | Tang et al. |

FOREIGN PATENT DOCUMENTS

| | | |
|---|---|---|
| DE | 33 11 811 A1 | 10/1984 |
| DE | 36 29 353 C1 | 1/1988 |
| DE | 40 34 611 A1 | 5/1992 |
| DE | 94 09 231.1 U1 | 12/1994 |
| DE | 200 18 593 U1 | 2/2001 |
| DE | 10017193 A1 | 11/2001 |
| DE | 202 02 906 U1 | 6/2002 |
| DE | 10 2005 007 773 A1 | 9/2005 |
| EP | 0 097 901 A2 | 1/1984 |
| EP | 0 258 928 A1 | 3/1988 |
| EP | 0 439 950 A1 | 8/1991 |
| EP | 0 885 623 A2 | 12/1998 |
| EP | 1 005 878 A2 | 6/2000 |
| EP | 1 138 341 A2 | 10/2001 |
| EP | 1 197 237 | 4/2002 |
| EP | 1 479 404 A2 | 11/2004 |
| EP | 1 514 570 A2 | 3/2005 |
| EP | 1 491 226 B1 | 1/2006 |
| EP | 1 197 237 B1 | 1/2007 |
| GB | 2 277 689 A | 11/1994 |
| GB | 2 338 420 | 12/1999 |
| GB | 2 338 420 A | 12/1999 |
| JP | 57-101952 | 6/1982 |
| JP | 59-151967 | 8/1984 |
| JP | 5-71790 A | 3/1993 |
| JP | 5-317428 A | 12/1993 |
| JP | 8-61731 A | 3/1996 |
| JP | 9-234247 A | 9/1997 |
| JP | 10-179746 | 7/1998 |
| JP | 11-57009 A | 3/1999 |
| JP | 2001-314508 A | 11/2001 |
| JP | 2002-95751 A | 4/2002 |
| JP | 2002-286677 A | 10/2002 |
| JP | 2003-245353 | 9/2003 |
| JP | 3673402 B2 | 4/2005 |
| JP | 2005-537083 A | 12/2005 |
| JP | 2007-518451 A | 7/2007 |
| JP | 2008-510510 A | 4/2008 |
| JP | 2008-541830 A | 11/2008 |
| JP | 2009-511218 A | 3/2009 |
| SU | 379270 | 4/1973 |
| WO | 86/02566 | 5/1986 |
| WO | 97/47348 | 12/1997 |
| WO | 97/47348 A1 | 12/1997 |
| WO | WO 98/04311 A1 | 2/1998 |
| WO | WO 00/21602 A1 | 4/2000 |
| WO | 2000/027457 | 5/2000 |
| WO | 01/10489 A2 | 2/2001 |
| WO | WO 01/13981 A1 | 3/2001 |
| WO | 03/018096 A1 | 3/2003 |
| WO | WO 03/055554 A1 | 7/2003 |
| WO | 2004/011072 A1 | 2/2004 |
| WO | 2004/020031 A1 | 3/2004 |
| WO | 2004/043528 | 5/2004 |
| WO | WO 2004/039444 A1 | 5/2004 |
| WO | 2004/105848 A1 | 12/2004 |
| WO | 2004/112873 A1 | 12/2004 |
| WO | 2005/011556 A2 | 2/2005 |
| WO | 2005/021076 A2 | 3/2005 |
| WO | 2005/079898 A2 | 9/2005 |
| WO | 2005/079898 A3 | 9/2005 |
| WO | WO 2005/079898 A2 | 9/2005 |
| WO | 2006/015416 | 2/2006 |
| WO | 2006/019323 A1 | 2/2006 |
| WO | 2007/045017 A2 | 4/2007 |
| WO | 2007/051230 A1 | 5/2007 |
| WO | 2007/101298 A1 | 9/2007 |
| WO | WO 2008/148154 A1 | 12/2008 |
| WO | WO 2009/015410 A1 | 2/2009 |

OTHER PUBLICATIONS

Third Office Action dated Jul. 25, 2017 issued in Chinese Application No. 201510085059.X with English translation (9 pages).
Office Action dated Mar. 24, 2017 issued in Chinese Application No. 201410543100.9 with English translation (19 pages).
First Examination Report dated May 18, 2017 issued in New Zealand Application No. 731691 (2 pages).
Communication dated May 18, 2017 issued in New Zealand Application No. 625603 (2 pages).
Statutory Declaration of Alex Young in the matter of New Zealand Application No. 625603 in the name of ResMed Limited and in the matter of an Opposition thereto by Fisher & Paykel Healthcare Limited (16 pages).
Translation of DE 100 17 193 A1.
Certificate of Translation of DE 100 17 193 A1.
Office Action dated Jan. 26, 2017 issued in Chinese Application No. 201510085059.X with English translation (16 pages).
Extended Search Report dated Feb. 24, 2017 issued in European Application No. 12162240.1 (12 pages).
Notice of Reasons for Rejection dated Mar. 11, 2014 in Japanese Application No. 2009-053840, with English translation (7 pages).
Notification of the Fourth Office Action dated Jul. 9, 2014 in Chinese Application No. 200910138707.8, with English translation (18 pages).
Decision of Rejection dated Nov. 2, 2014 issued in Chinese Application No. 200910138707.8 with English translation (22 pages).
First Patent Examination Report dated Jun. 26, 2015 issued in Australian Application No. 2014204454 (2 pages).
First Examination Report dated Nov. 18, 2015 issued in New Zealand Application No. 714075 (3 pages).

(56) References Cited

OTHER PUBLICATIONS

Notice of Reasons for Rejection dated Feb. 8, 2016 issued in Japanese Application No. 2014-255952 with English translation (6 pages).
Notification of Reexamination dated Mar. 3, 2016 issued in Chinese Application No. 200910138707.8 with English translation (25 pages).
Notification of the First Office Action dated Mar. 14, 2016 issued in Chinese Application No. 201410543100.9 with English translation (21 pages).
Notice of Opposition to Grant of Patent filed Mar. 29, 2016 filed by Fisher & Paykel Healthcare Ltd. (2 pages).
Statement of Case filed May 25, 2016 filed by Fisher & Paykel Healthcare Ltd. (19 pages).
First Amended Notice of Opposition filed May 25, 2016 filed by Fisher & Paykel Healthcare Ltd. (2 pages).
Evidence of Prior Publication file May 25, 2016 filed by Fisher & Paykel Healthcare Ltd. (3 pages).
Notification of the First Office Action dated Jun. 2, 2016 issued in Chinese Application No. 201510085059X with English translation (8 pages).
Notification of Reexamination dated Aug. 3, 2016 issued in Chinese Application No. 200910138707.8 with English translation (22 pages).
Notice of Allowance dated Aug. 15, 2016 issued in Japanese Application No. 2014-255952 (3 pages).
Second Office Action dated Nov. 30, 2016 issued in Chinese Application No. 2014105343100.9 with English translation (18 pages).
Decision of Reexamination dated Nov. 15, 2016 issued in Chinese Application No. 200910138707.8 with English translation (45 pages).
Deadline for Counterstatement mailed Oct. 31, 2013 in New Zealand Application No. 595304, together with Statement of Case dated Oct. 16, 2013 and Amended Notice of Opposition to Grant of Patent (12 pages).
Notification of the Third Office Action dated Dec. 23, 2013 in Chinese Application No. 200910138707.8 with English translation (9 pages).
First Examination Report dated Dec. 20, 2012 in New Zealand Application No. 604137 (2 pages).
Notice of Reasons for Rejection dated May 7, 2013 in Japanese Application No. 2009-053840 with English translation (14 pages).
Patent Examination Report No. 1 dated Mar. 19, 2013 in Australian Application No. 2009200879 (4 pages).
Notification of the Second Office Action dated Jun. 5, 2013 in Chinese Application No. 200910138707.8 with English translation (21 pages).
Notification of First Office Action dated Sep. 18, 2012 in Chinese Application No. 200910138707.8 with English translation (21 pages).
Wiest et al., "In Vivo Efficacy of Two Heated Humidifiers Used During CPAP-Therapy for Obstructive Sleep Apnea Under Various Environmental Conditions," Sleep, vol. 24., No. 4, 2001, Abstract.
Fairchild Semiconductor, "MM74HC74A Dual D-Type Flip-Flop with Preset and Clear," Sep. 1983 (Revised Jan. 2005), pp. 1-8.
TelCom Semiconductor, Inc., "3-Pin μP Reset Monitors," TCM809/810-04, Aug. 29, 1996, pp. 5-15 through 5-18.
Unitrode Products from Texas Instruments, "Current Mode PWM Controller," SLUS224A, Sep. 1994 (Revised Apr. 2002), 11 pages.
National Semiconductor Corporation, "LP339 Ultra-Low Power Quad Comparator," DS005226, Aug. 2000, pp. 1-12.
Extended European Search Report dated Jul. 21, 2009 in corresponding European Appln. No. 09003338.2 (9 pages).
Dec. 6, 2018 First Examination Report issued in New Zealand Application No. 748308.
Office Action dated Jul. 6, 2018 issued in European Application No. 12162240.1 (7 pages).
Notice of Reasons for Rejection dated Mar. 5, 2018, issued in Japanese Application No. 2016-175411 with English translation (13 pages).
Nov. 16, 2006 International Search Report for PCT/AU2006/001173.
U.S. Appl. No. 60/707,948, filed Aug. 15, 2005 (pg. 11 of the specification).
U.S. Appl. No. 60/707,949, filed Aug. 15, 2005 (pg. 9 of the specification).

* cited by examiner

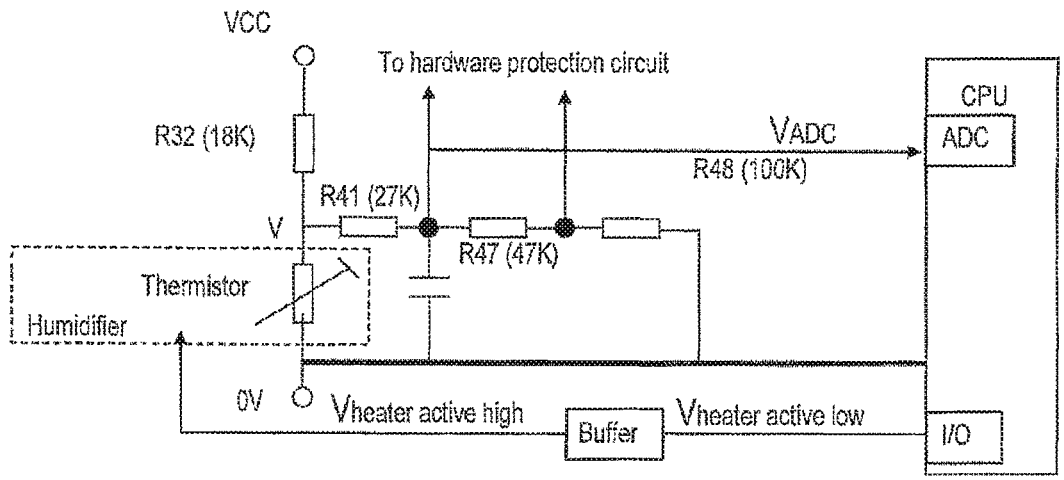
Fig. 13.1
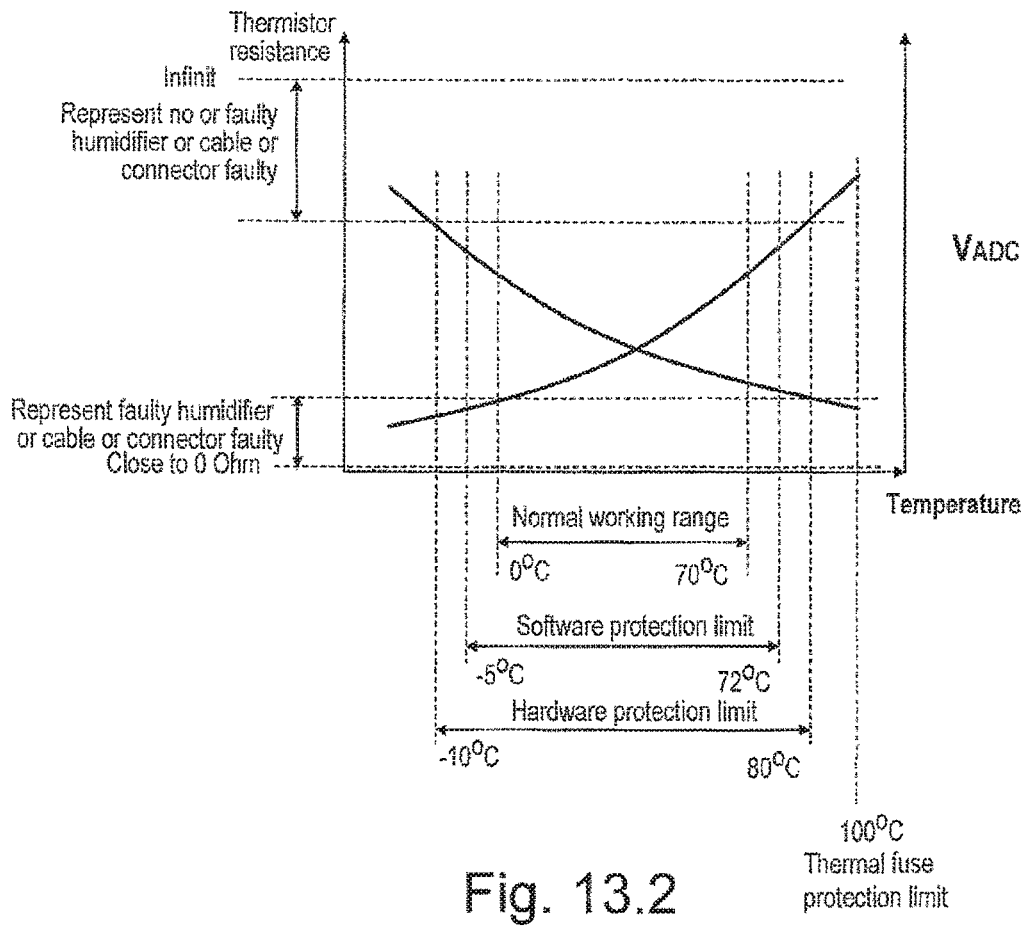
Fig. 13.2

| Va | Vb | Vc | V (reference to 0V) |
|---|---|---|---|
| 0V | 0V | 0V | V1 = 0V |
| 0V | 5V | 0V | V2 = 1V |
| 5V | 0V | 0V | V3 = 2V |
| 5V | 5V | 0V | V4 = 3V |

Fig. 17

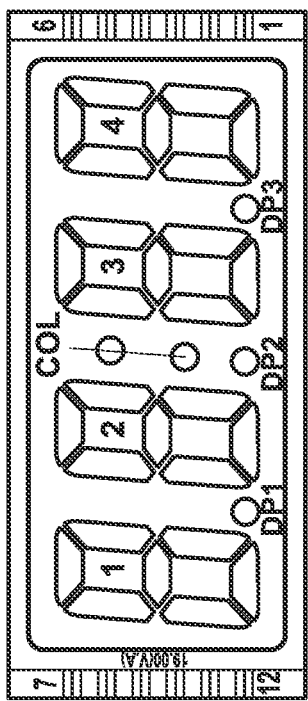
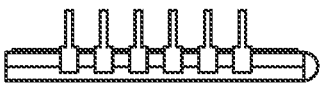
Fig. 18-1                Fig. 18-2
Fig. 18-3
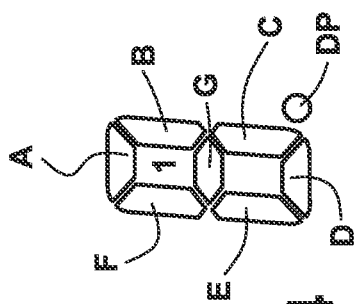
Fig. 18-4
| PIN | 1 | 2 | 3 | 4 | 5 | 6 | 7 | 8 | 9 | 10 | 11 | 12 |
|---|---|---|---|---|---|---|---|---|---|---|---|---|
| COM0 | | | | COM0 | 4B | 4A | 3B | 3A | 2B | 2A | 1B | 1A |
| COM1 | | | COM1 | | 4G | 4F | 3G | 3F | 2G | 2F | 1G | 1F |
| COM2 | | COM2 | | | 4C | 4E | 3C | 3E | 2C | 2E | 1C | 1E |
| COM3 | COM3 | | | | DP2 | 4D | DP3 | 3D | COL | 2D | DP1 | 1D |
Fig. 18-5

LOW COST CPAP FLOW GENERATOR AND HUMIDIFIER ASSEMBLY

CROSS-REFERENCE TO PRIORITY APPLICATION

This application is a divisional of U.S. application Ser. No. 13/890,302, filed May 9, 2013, which is a divisional of U.S. application Ser. No. 11/988,934, filed Jan. 17, 2008, which is the U.S. national phase of International Application No. PCT/AU2006/001173 filed Aug. 15, 2006, which designated the U.S. and claims priority to U.S. Provisional Application No. 60/707,951 filed Aug. 15, 2005, each incorporated herein by reference in its entirety.

BACKGROUND OF THE INVENTION

Field of the Invention

The present invention relates to a low cost Continuous Positive Airway Pressure (CPAP) device used to treat sleep disordered breathing (SDB) conditions such as Obstructive Sleep Apnea (OSA). In particular, the present invention relates to a low cost CPAP flow generator and humidifier assembly.

Background of the Invention

Since Sullivan's invention of nasal CPAP treatment of "snoring sickness", treatment systems have become quieter and more comfortable for patients. Typically, a patient is tested by a sleep physician who titrates a treatment pressure for the patient, and the patient is sent home with a basic low-cost CPAP device that is set to, and remains at, that treatment pressure. While more sophisticated devices exist that can to some extent automatically titrate, the majority of patients are treated with a basic low-cost CPAP device. A basic CPAP device comprises a blower that can provide a supply of air or breathable gas at pressures in the range of 4 $cmH_2$ to 20 $cmH_2O$. There is a constant need in the art to reduce cost while providing the same functionality.

A common configuration of a treatment system comprises a CPAP device and a patient interface, typically a nasal mask. The nasal mask forms a sealing interface with the patient's nasal passages in use so that the supply of air at positive pressure from the CPAP device is delivered to the patient's airways. While the patient is wearing a nasal mask, their mouth is uncovered.

In some situations, patients "mouth breath" during sleep. When this happens while wearing only a nasal mask, air can pass in the mask and straight out the mouth. This can lead to drying of the airway and patient discomfort. This patient discomfort can to some extent be alleviated by the use of a humidifier placed between the CPAP device and patient interface.

Many humidifiers are available, although the most convenient form is one that is either integrated with or configured to be coupled to the relevant CPAP device. While passive humidifiers can provide some relief, generally a heated humidifier is required to provide sufficient moisture to the air so that patients will be comfortable. Humidifiers typically comprise a water tub having a capacity of several hundred milliliters, a heating element, a control to enable the level of humidification to be varied, an air inlet to receive air from the blower, and an air outlet adapted to be connected to an air delivery conduit so that the humidified pressurized air may be passed to the patient interface. Usually, the water tub is removable from the system so that it can be refilled when necessary.

Often patients may start with a CPAP flow generator/blower and later desire to include a humidifier. However, not all patients require humidification. Thus there is a commercial advantage in having a system that allows a patient to start with a flow generator and later choose to upgrade to a humidifier at low cost.

The cost of producing equipment is influenced by a number of factors including parts, labor, factory overhead, packaging, transport, and distribution costs and taxes. Labor costs can be reduced in a number of ways, such as by designing for simple, low cost manufacture. For example, a design that calls for fewer parts is quicker, simpler and cheaper to manufacture. A design that uses cheaper parts is likewise cheaper overall.

There is a spectrum of humidifier/CPAP device coupling configurations from fully integrated to completely separate. In between these end points, there is a range of intermediate configurations.

Moreover, peripheral components such as a humidifier can be more expensive since they typically include hardware and other expensive components and controls which are necessary for communication with the basic CPAP device.

By way of example, in a completely separate configuration there is only a hose delivering a supply of air at positive pressure between the CPAP device and humidifier, and there are no electrical signals between the two devices, such as control or sensing signals. While the CPAP device might be able to discriminate the presence of the humidifier by an increase air impedance on the hose, there is no signal sent between the two devices to advise the CPAP device of the presence of the humidifier. Furthermore, all heating and humidification controls reside on the humidifier. Power must be separately supplied to the humidifier. An example of such a humidifier is the ResMed HUMIDAIRE™ humidifier.

An example of a system using an intermediate configuration is ResMed's S7 CPAP device. In this system, the CPAP device can be used without any humidifier. However, if the front panel of the CPAP device is removed, a specific humidifier, e.g., the ResMed H2I™ humidifier, may be connected. There are a number of electrical and mechanical connections between the CPAP device and humidifier. Power for the heater is supplied from the CPAP device and hence there is no separate power cord for the humidifier. Humidification controls reside on the humidifier.

In a fully integrated system, the humidifier is not removable from the CPAP device (although the humidifier tub may be removable to facilitate refilling).

Other known systems include Fisher & Paykel's PCT Application no. WO2004/043528 and Respironics' RemStar AUTO product.

In summary, there is a need in the art to provide a basic low-cost CPAP device which is upgradeable with a suitable humidifier.

BRIEF SUMMARY OF THE INVENTION

One aspect of the invention is to provide a low-cost CPAP flow generator/blower and humidifier assembly. Another aspect of the invention is to provide a CPAP flow generator/blower that has an optional low-cost upgrade to humidification. Another aspect of the invention is to provide a CPAP flow generator/blower and humidifier assembly in which humidification control is provided on the flow generator rather than on the humidifier or humidifier tub. The humidifier tub may be detachable from the flow generator and/or the common support cradle.

Another aspect of the invention relates to a low-cost CPAP having software based control of a humidifier having a tub that may be detachable from the flow generator, e.g., using the same microprocessor of the CPAP for multiple tasks—multi tasking and resource sharing of one CPU— such as CPAP motor and/or therapy control, humidifier detection and/or control and/or user interface control.

Another aspect relates to the provision of a CPAP device with reduced componentry but without the sacrifice of reduced functionality.

Another aspect relates to a low-cost, low-memory capacity microprocessor for a CPAP device which is configured to control one or more auxiliary components via software based control.

Another aspect relates to a CPAP device including native control systems, e.g., based on software, for later added components or accessories, such as a humidifier. Such a control system can take the form of code that is written in the CPAP device's microprocessor. The code of controlling the humidifier can take up as little as 100-150 bytes of memory.

Another example of the invention relates to a low cost and easy to use humidifier. The humidifier/tub need not include a control system or even control knobs, the operation and/or functionality of each of which may be provided in a CPAP device instead. Further, the humidifier/tub can simply include low power and low cost switches. In a preferred embodiment the power control switch is on the humidifier/tub but the software control of this switch is in the flow generator. This design ensures that the cost of the switch is carried by the humidifier/tub and not the flow generator. There is minimal additional cost to the flow generator in having the software control of the humidifier incorporated in the flow generator.

In one example, the invention includes a CPAP device wherein humidification control is performed by a microprocessor of the CPAP device without requiring a separate humidification control processor. Motor control and display control can be performed by the microprocessor without requiring a separate motor control processors and display control processors.

In another example, a CPAP device comprises a flow generator including a microprocessor with an analog-to-digital converter (ADC); a humidifier tub detachably coupled to the flow generator; and a temperature sensor in communication with the humidifier and adapted to produce a signal (voltage is an example of a signal that may be provided to the flow generator, but other types of signals such as a current signal or an optical signal may also be used) provided to the flow generator microprocessor via the ADC, wherein the microprocessor is programmed with a humidifier control program to control power supply to the humidifier in accordance with output of the temperature sensor. The ADC can be built in to the microprocessor, or it can be an external component.

In still another example, a method for controlling a humidifier of a CPAP device, comprises monitoring the temperature of the humidifier; generating a signal, e.g., a voltage signal, representative of the humidifier temperature; converting the signal to a digital value; applying the digital value to a microprocessor of a flow generator of the CPAP device; and supplying power to the humidifier in accordance with the digital value.

In still another example, a method for detecting and identifying a valid humidifier of a CPAP device comprises monitoring the temperature sensor output of the humidifier; generating a signal, e.g., a voltage signal, representative of the humidifier temperature; converting the signal to a digital value; applying the digital value to a microprocessor of a flow generator of the CPAP device; and enabling or disabling the humidifier function. A further aspect of the method may be to provide a message to the user, e.g., provide "new-user" interface for humidifier operation, in which case the humidifier and/or blower will provide instructions suited for a novice user. Alternatively or in addition, the message may warn the user of a non-valid humidifier or fault condition in accordance with the digital signal. The message may also include an indication or signal that the humidifier is valid, e.g., the message may include one or more of the following: a) "correct humidifier is connected", b) "the connection of the humidifier is correct" and/or c) "the humidifier is functional". In one embodiment the indication may be in the form of a light emitting diode (LED) that signals the attachment and functioning of a valid humidifier.

According to another example of the invention, there is provided a CPAP device comprising a flow generator including a microprocessor, a motor provided to the said flow generator, and a digital circuit to detect RPM of the motor, said digital circuit including a clock timer, a counter unit and a decoder, wherein the decoder is configured to generate a signal that is indicative of RPM as a function of time. Another example of the invention covers the analog method of monitoring and optionally controlling motor speed (RPM).

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 13.1 is a circuit for humidifier detection and/or control according an embodiment of the present invention;

FIG. 13.2 is a graph illustrating values that can be utilized by the microprocessor software as an indication of the operation state and/or presence of the humidifier;

FIG. 17 is a chart showing logic signal combinations for use with the driving circuit of FIG. 16;

FIGS. 18-1, 18-2, 18-3, 18-4, 18-5, 19, and 20 illustrate details of an example of an LCD according to an embodiment of the present invention;

DETAILED DESCRIPTION OF THE INVENTION

1. Overall CPAP System

Figure 1:
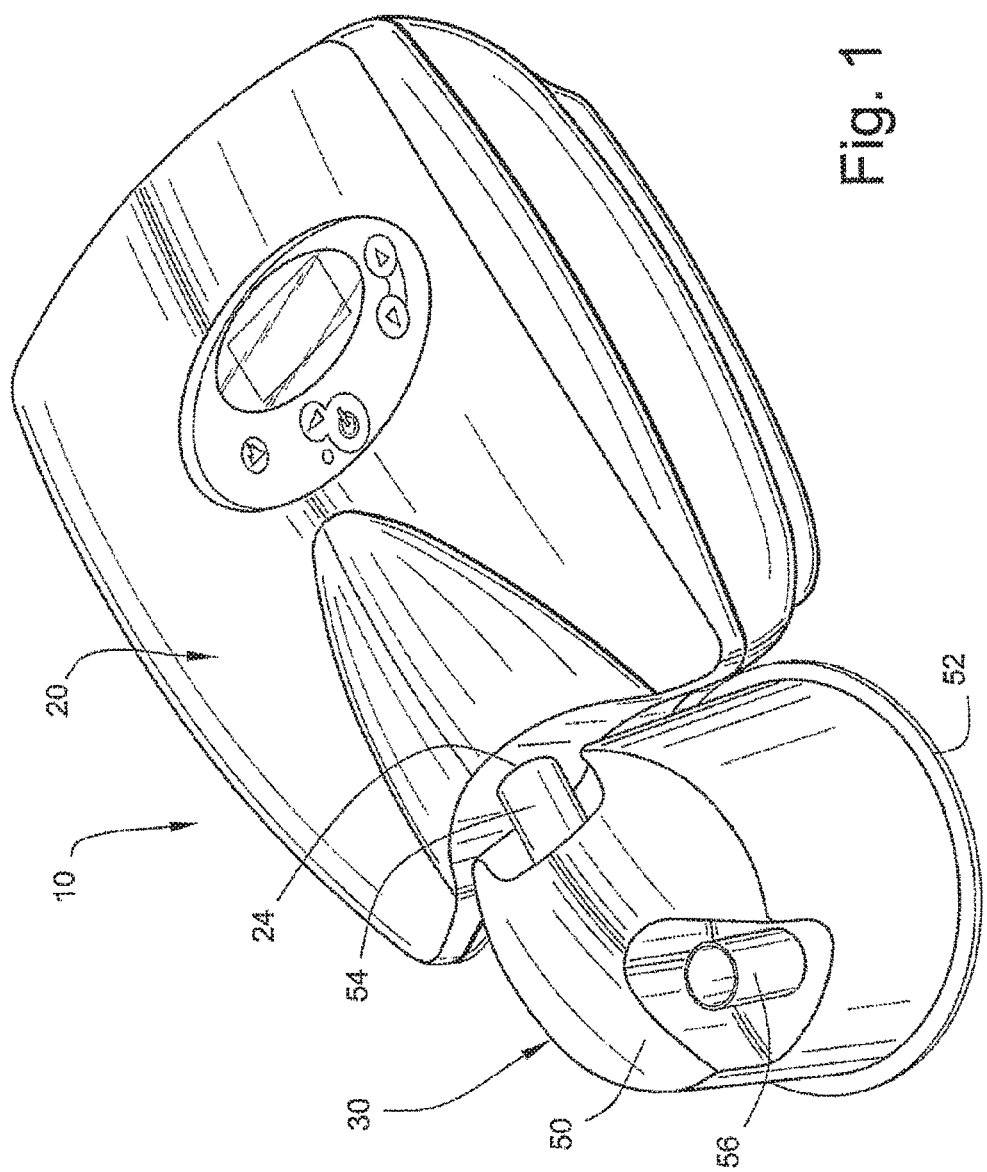
FIG. 1 is a perspective view of a CPAP device according to an embodiment of the invention.

FIGS. 1-4 illustrate a CPAP system 10 according to an embodiment of the present invention. As illustrated, the CPAP system 10 includes a flow generator 20 and a heated humidifier 30 adapted to be coupled to the flow generator 20. The CPAP system 10 provides a low cost system having a simplified functionality, a reduced electronics and mechanical parts count, and low cost manufacture design.

2. Humidifier

In heated humidification, air from the flow generator/ blower outlet is directed over a body of heated water picking up moisture before exiting the humidifier tub. The water is heated by being in thermal contact with a heating element. Typically control of the electrical circuit that controls the heating element resides in the humidifier. However in the present example, the control processor and most control circuitry parts reside in the flow generator.

The humidifier 30 includes a humidifier tub 50 having a base plate 52 sealed to the bottom of the tub 50. The tub 50 includes an inlet 54 adapted to be in fluid communication with (but not necessarily directly) the outlet 24 of the flow generator 20, and an outlet 56 adapted to be connected to an air delivery conduit. The air delivery conduit includes one end coupled to the outlet 56 of the tub 50 and an opposite end coupled to a patient interface. The patient interface comfortably engages the patient's face and provides a seal. The patient interface may have any suitable configuration as is known in the art, e.g., full-face mask, nasal mask, oronasal mask, mouth mask, nasal prongs, etc.

The tub 50 and base plate 52 define a chamber that is adapted to receive a volume of water, e.g., several hundred milliliters (e.g., 200-500 mL). The inlet 54 and the outlet 56 are both in communication with the chamber. In use, a supply of pressurized air from the flow generator 20 enters the inlet 54 of the tub 50 and collects moisture through contact with the heated water within the tub 50 before continuing on to the outlet 56 and to the patient via the air delivery conduit.

Figure 2:
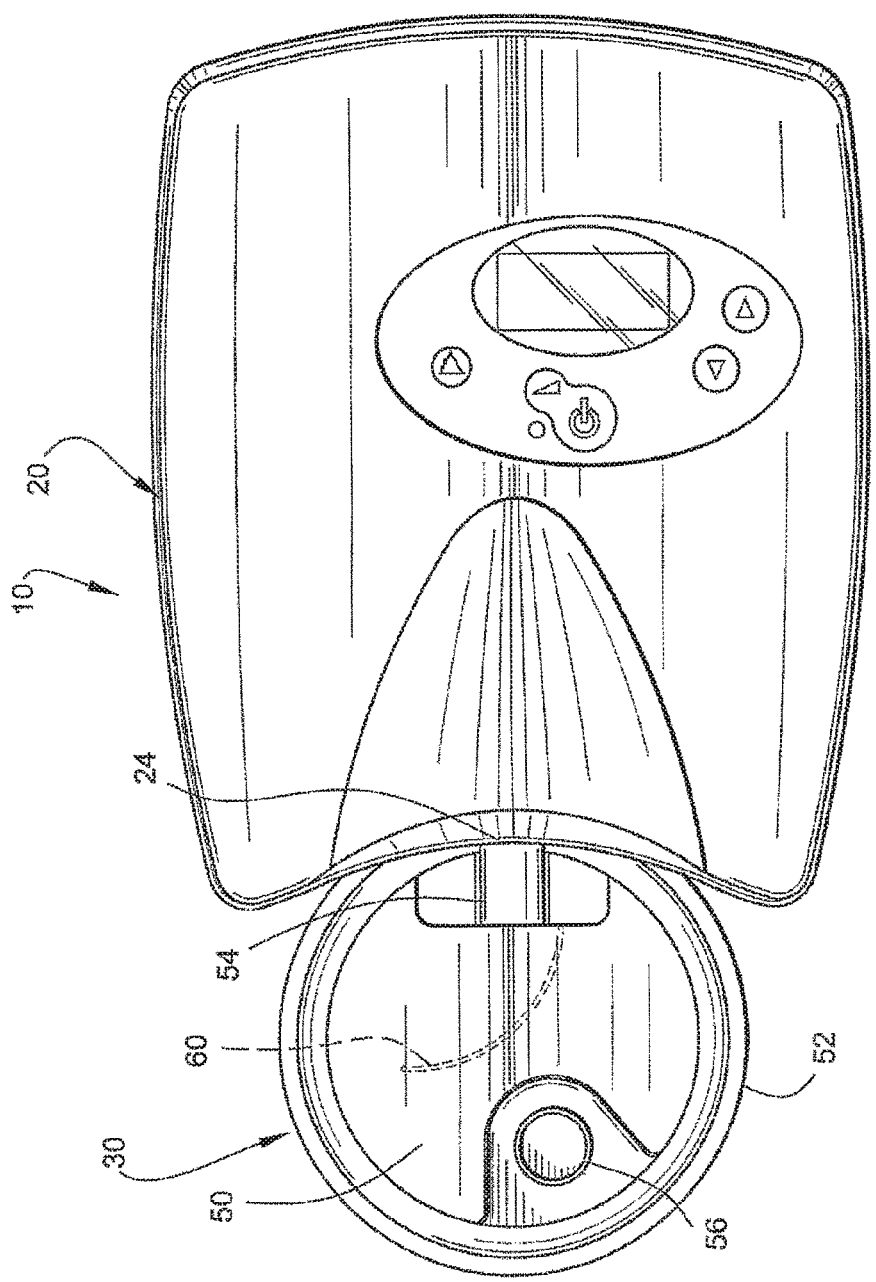
FIG. 2 is a top view of the CPAP device shown in FIG. 1.
Figure 3:
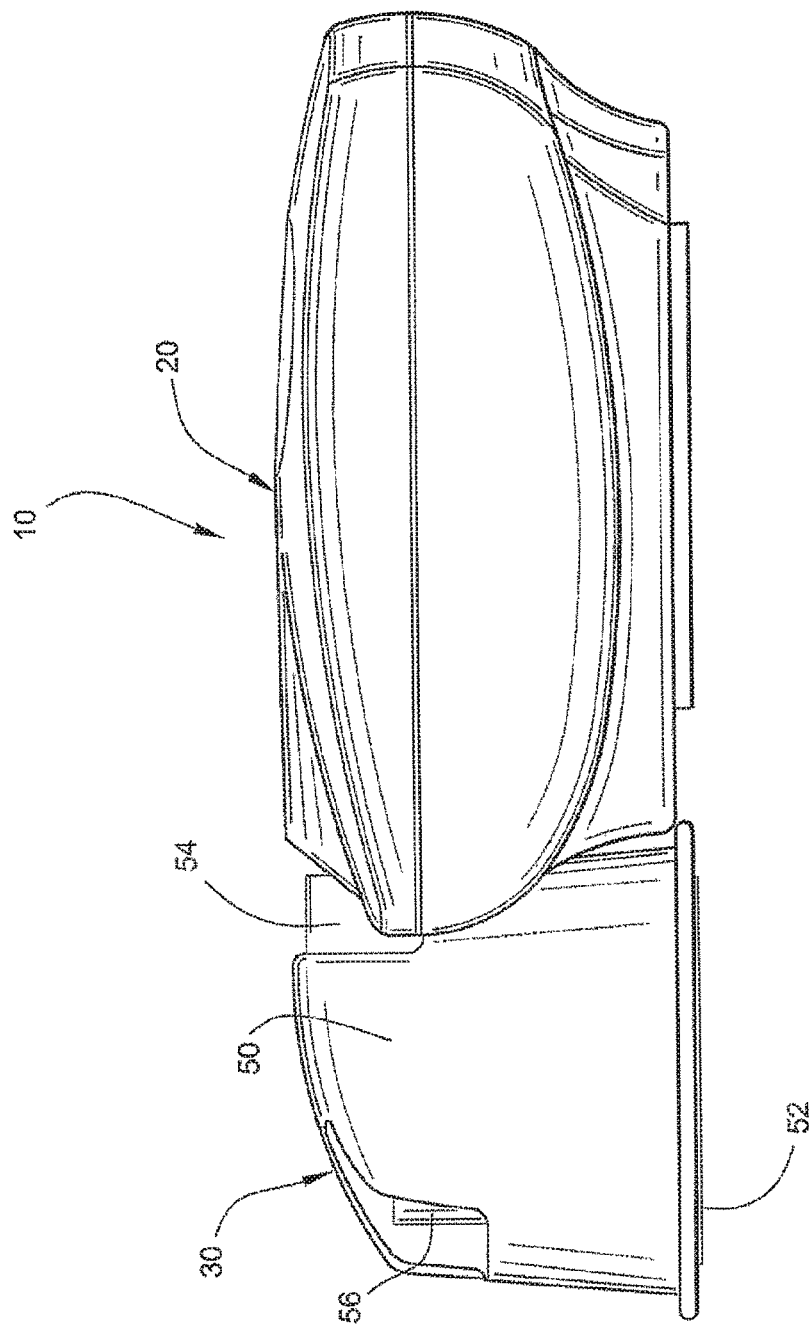
FIG. 3 is a side view of the CPAP device shown in FIG. 1.
Figure 4:
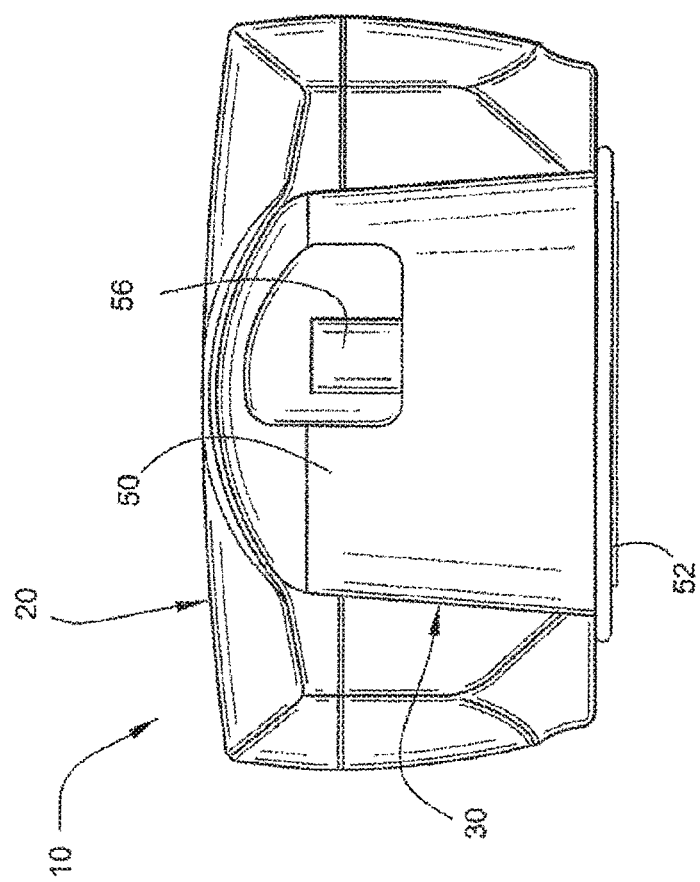
FIG. 4 is an end view of the CPAP device shown in FIG. 1.

As best shown in FIG. 2, the tub 50 may include a curved baffle 60 adjacent the outlet end of the inlet 54 to smoothly change the direction of the air flow by gently guiding the air flow around the tub 50 while limiting the loss of pressure. Also, the base plate 52 may be in the form of a heat conducting base plate. Specifically, the base plate 52 may be formed of a heat conducting material, e.g., aluminum sheet.

In an embodiment, the humidifier tub 50 may be structured such as the humidifier described in commonly-owned U.S. Provisional Patent Application No. 60/707,949, entitled "Humidifier Tub For CPAP Device", filed Aug. 15, 2005, the contents of which are incorporated in its entirety by reference herein.

3. Cradle

Figure 5:
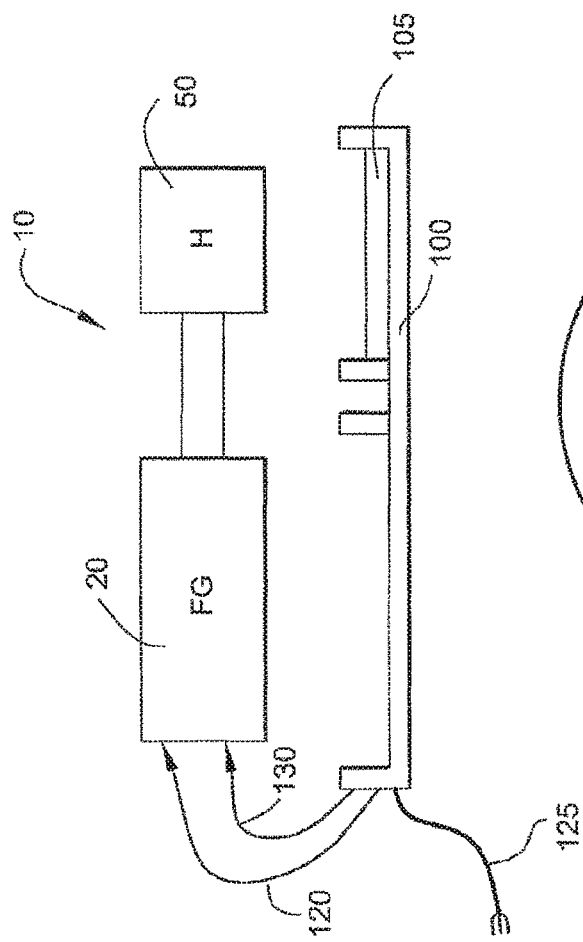
FIG. 5 is a schematic diagram of an assembly including a CPAP device, a humidifier and a cradle according to an embodiment of the invention.

As schematically illustrated in FIG. 5, the CPAP device 10 may include a cradle 100 structured to support the humidifier tub 50 in an operative position with respect to the flow generator 20.

Figure 6:
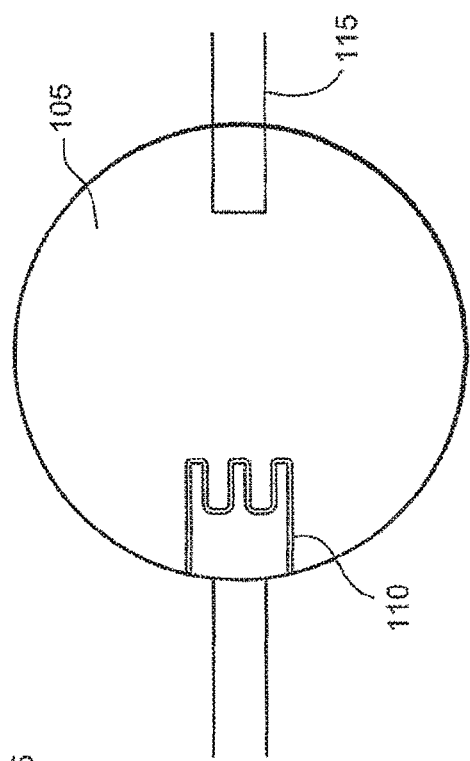
FIG. 6 is a schematic diagram of a heater plate according to an embodiment of the invention.

The cradle 100 may include a heater plate 105 that includes a heating element 110 as schematically illustrated in FIG. 6, e.g., a ceramic heating element. In use, the cradle 100 receives the humidifier tub 50 so that the heating element 110 is in thermal contact with the heat conducting base plate 52 (FIG. 3) of the humidifier tub 50. This arrangement allows water contained within the humidifier tub 50 to be heated to provide sufficient moisture to the air so that patients will be comfortable.

In an alternative, the heater element could be integrally formed with or otherwise associated with the humidifier tub 50. For example, the heater element could include a ribbon heater placed inside the tub and in communication with a power source. Such ribbon or Thermofoil heaters are commercially available, e.g., from Mod-Tronics Instruments, Limited.

3.1 Cradle Electrical Design

Temperature sensing is preferably performed by a thermistor 115 (FIG. 6), e.g., having 33K resistance at room temperature and 1% tolerance. The cradle 100 includes a signal cable 120, an alternating current (AC) power inlet cable 125, and an AC outlet cable 130. In use, the signal cable conducts three signals between the cradle and the flow generator, i.e., a temperature sensor signal, a power signal, and a ground signal. The AC inlet cable is connected to a main power supply, and the AC outlet cable is connected to an AC inlet socket on the flow generator thereby providing power to it. Control of the heating element is performed by the flow generator Central Processing Unit (CPU) as will be described below. In this way, the electrical design of the cradle is relatively simple and inexpensive.

4. Flow Generator

The flow generator may be a stand-alone device that produces a supply of air at positive pressure, e.g., in the range of 4 to 20 cmH$_2$O. The flow generator includes an electric motor that drives an impeller, a volute, a display, a power supply, a printed circuit board (PCB), and a housing. The housing provides an air inlet and an air outlet that may be directly or indirectly connected to an air delivery conduit and hence to a patient interface. When a humidifier is used, it is generally placed between the air outlet of the flow generator and the air delivery conduit as described above. As is known in the art, the impeller is operable to draw a supply of air into the housing through the air inlet and provide a pressurized flow of air at the air outlet.

4.1 Flow Generator Mechanical Design

In accordance with an aspect of the present invention, while the humidifier is a separate component from the flow generator, humidification control is performed by the flow generator. The mechanical connection between the humidifier and flow generator is relatively simple and can be relatively imprecise, in terms of axis alignment of the sealing elements on the flow-generator outlet and water tub, when compared to other known systems such as the ResMed S7 CPAP device and H2i humidifier. See, e.g., commonly-owned, U.S. Provisional Application No. 60/707,948, filed Aug. 15, 2005, entitled "REMOVABLE HUMIDIFIER FOR CPAP DEVICE" and incorporated herein by reference in its entirety.

4.2 Flow Generator Electrical Design

Figure 7:
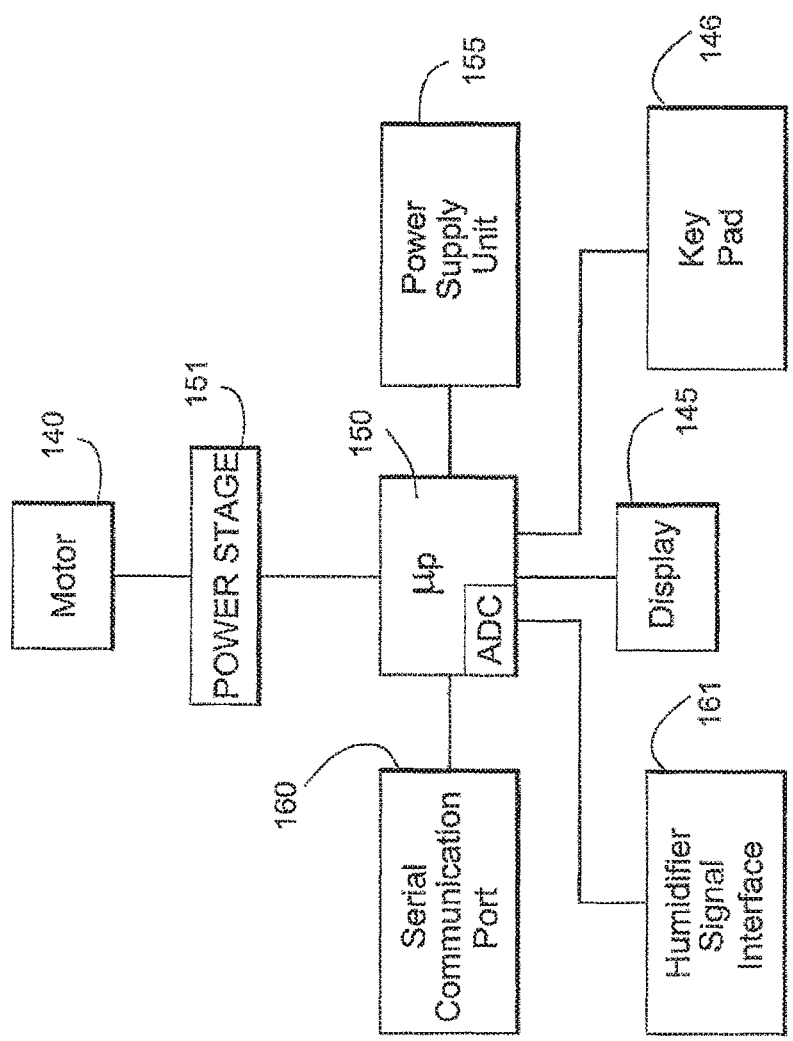
FIG. 7 is a schematic block diagram showing major electrical components of a CPAP device according to an embodiment of the invention.
Figure 8:
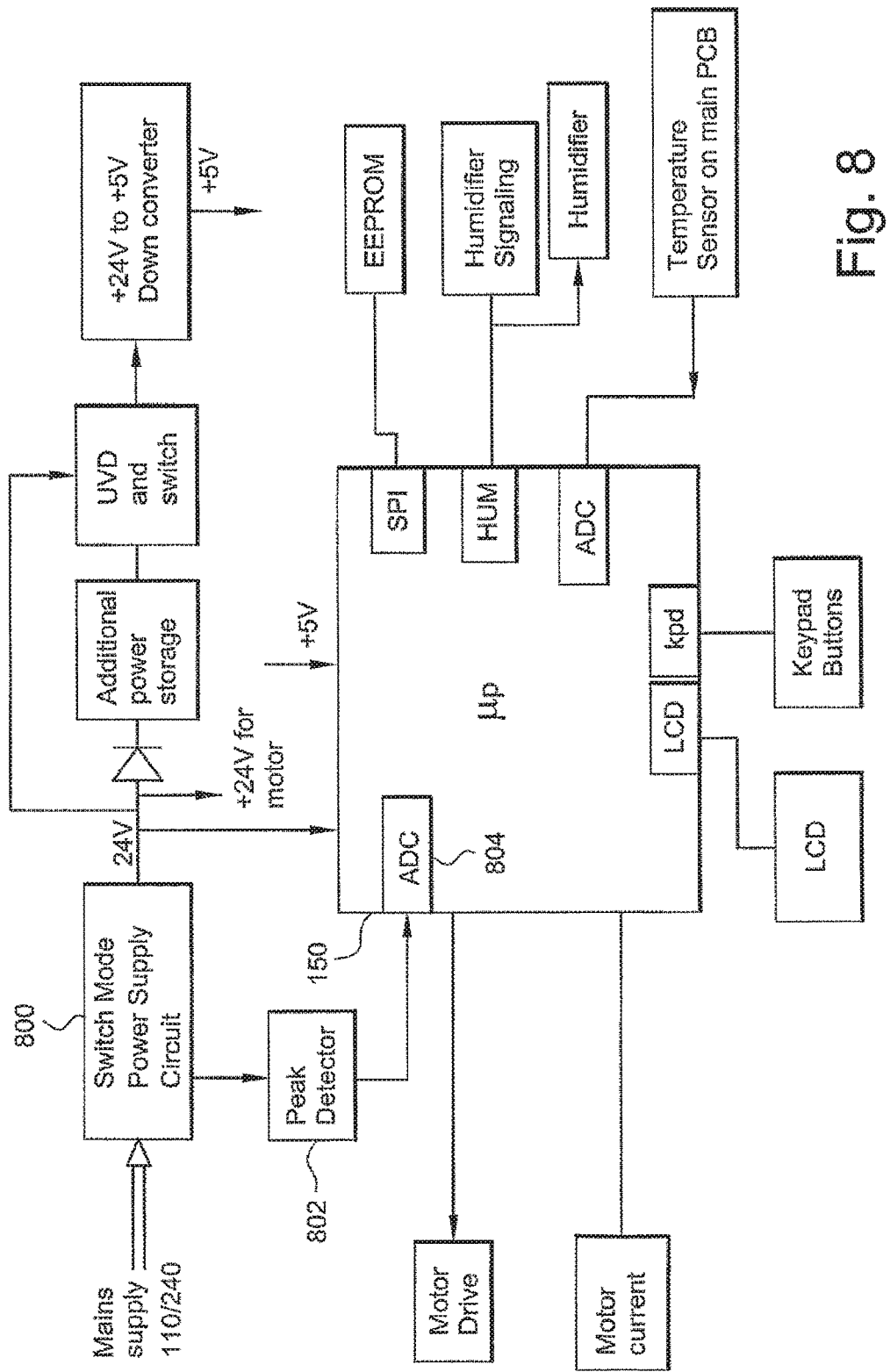
FIG. 8 is a block diagram showing an example of a more complete complement of components of a CPAP device according to an embodiment of the present invention.

As schematically illustrated in FIG. 7, the main portions of the flow generator electrical design include a motor 140, a display 145, e.g., a 7 segment LCD Display, a key pad 146, a low cost microprocessor 150, a motor driving power stage 151, a space power supply unit (PSU) 155, a communications signal port 160, and a humidifier signal interface 161. In one embodiment, the microprocessor does not drive the motor directly, the microprocessor provides a driving logic signal to the power stage and then the power stage provides the power to drive the motor. While FIG. 7 shows exemplary main portions of the flow generator electrical design, FIG. 8 shows an example including a more complete complement of flow generator electrical components.

In known devices, the motor commutation and safety control and the display control are performed by separate integrated circuits. For example, the motor control is performed by a Motorola integrated circuit (IC), e.g., processor, and the display control is performed by an IC, e.g., a costly customized LCD driver IC embedded in an off-the-shelf LCD module, e.g., the Hitachi HD44780U.

In contrast, the microprocessor 150 of the flow generator performs one and preferably both motor and display control functions. Bringing the motor control and LCD display control onto the microprocessor 150 reduces the number of electronic circuit parts and costs for the flow generator. In addition, as discussed in more detail below, the microprocessor 150 performs humidification control. Further, many functions traditionally performed by circuit hardware are being performed by software in the flow generator 150. A challenge that this approach creates is additional work for the microprocessor 150 that may, in theory, require a high-powered microprocessor. However, as discussed in more detail below, all of these functions may be achieved with a relatively simple low powered microprocessor 150, e.g., the implementation memory requirements for the humidifier controller algorithm is between about 100-150 bytes.

One microprocessor that is commercially available is the ST-7, manufactured by ST-Microelectronics. There is a family of ST-7 microprocessors. One type of ST-7 microprocessor is currently used in a commercially available CPAP machine—the Kaerys KXS. However, the ST-7 microprocessor used in the Kaerys KXS is more expensive as it has a larger memory, 60K read only memory (ROM) and more input/output ports (I/O). The ST-7 used in the present invention is from the STM7 series, ST7FMC2R7T6, it is an 8 bit, 48K ROM and 1.5K RAM processor. In accordance with one aspect of the present invention, this processor can be used to record usage hours, although compliance data is not necessarily recorded and can be eliminated. An EEPROM can also be used to store motor hours. In addition, the microprocessor need not communicate with external devices (e.g., a PC, smart card, etc.), although various information can be accessed during manufacture and servicing.

4.3 Flow Generator Software Design

4.3.1 Humidifier Heating Control

A heated humidifier requires some form of control system that controls when electrical power is to be applied to the heater element. In particular, the control system should have a temperature set point or range, a temperature signal received from a temperature sensor, and a signal indicating when to activate/deactivate heating of the heater plate. Many different control schemes are possible.

Figure 9:
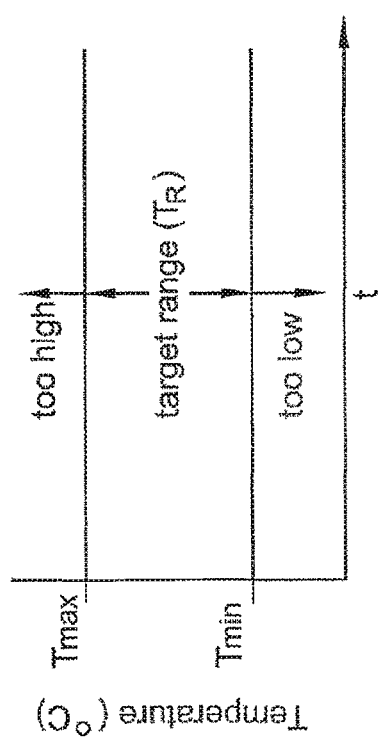
FIG. 9 is a graph illustrating a temperature target range defined by minimum and maximum temperatures.

In one example, the system has a valid operating range set between a minimum and maximum working temperatures, for example, 5° C. and 60° C., respectively. If the temperature of the heating element is detected to be below or above the valid operating range the heater plate is inactivated. However, under these conditions the humidifier may still be used with the system as an unheated passover humidifier but there will be no power supplied to the heating element. FIG. 9 is a graph which shows a target temperature range ($T_R$) which is defined between a minimum temperature ($T_{MIN}$) and a maximum temperature ($T_{MAX}$). In this example, the target range of the humidifier is between about 15-40° C. although other temperatures (less than 15° C. or greater than 40° C.) or other temperature ranges can be used as the target, depending on the specifics of the application. The control algorithm controls the temperature not only within the valid operating range (global max-min range) but within sub-ranges in that range e.g., the user may have a setting between 1 and X, for example 3. The operational range is then divided (not necessarily equally) into temperature sub-ranges where each sub-range corresponds to one setting. Thus there would be set $T_{MIN}$ and $T_{MAX}$ limits for each sub-range, called local temperature limits, as well as overall or global $T_{MIN}$ and $T_{MAX}$ limits. In this respect FIG. 9 corresponds to one sub-range. In another embodiment, $T_{MIN}$ and $T_{MAX}$ may also be equal to each other such that there is a single temperature value for each user setting and the control system monitors whether the temperature is at this temperature or not. If not, the heater is either turned off or on depending upon whether the temperature is above or below this set temperature.

Figure 10:
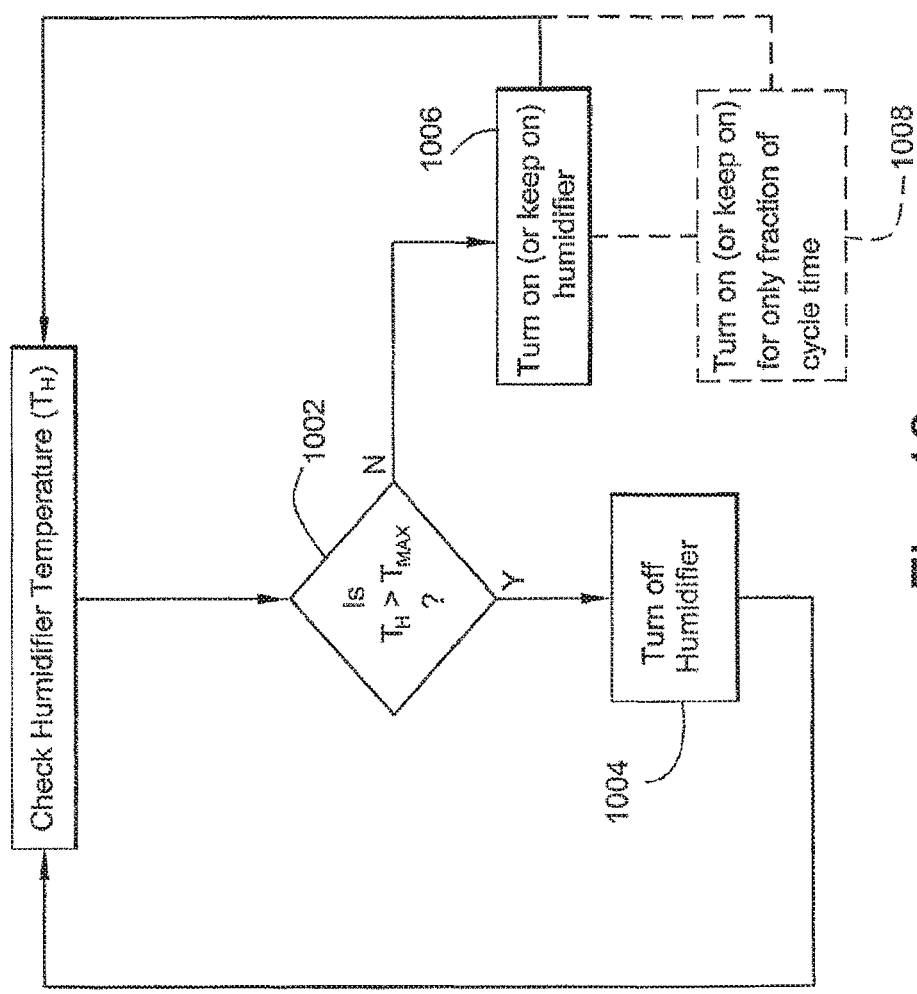
FIGS. 10 and 11 are program charts for controlling humidifier temperature according to embodiments of the invention.

FIG. 10 illustrates a simple algorithm for controlling the temperature of the humidifier ($T_H$). In Step 1002, a determination is made as to whether $T_H \geq T_{MAX}$. This determination is based on a water temperature sensed by the thermistor 115 (FIG. 6). If "Yes", a control signal is sent to turn off (discontinue or cut off power to) the heating element 110 in the humidifier (Step 1004). If it is determined that $T_H < T_{MAX}$, a signal is generated from the microprocessor 150 to turn on (or keep on) heating element in the humidifier (Step 1006).

Following Steps 1004 and 1006, the humidifier temperature $T_H$ is checked again to begin the cycle again of comparing to $T_{MAX}$, e.g., in the range of 1-10 seconds, such as every 1 second or 5 seconds. If at any time it is determined that $T_H \leq T_{MAX}$, then a signal is generated to supply power to the heating element of the humidifier. However, in accordance with a preferred aspect of the invention, power is supplied to the humidifier for only a fraction of the cycle time (Step 1008). For example, the heating element can then be regulated to heat up at a predetermined rate, e.g., not more than 5° C./second.

For example, if the cycle time is 1 second, the power is supplied to the humidifier for less than a second, e.g. 5%-95% or 10%-100% or 1%-99% of a second. The "duty cycle" is that portion or percentage of the cycle where power is supplied to the heating element while "temperature rising rate" is dependent upon the duty and the frequency of the duty. For example, if the duty is ¼ and the frequency is 1 second then power is applied to the heating element for 0.25 seconds of every 1 second. Use of a duty cycle is especially advantageous if the heating element 110 is sensitive to rapid power increases, or if the heating element is designed for use with a 110V power source, but can also be used with a 240V power source even though the 240V source would otherwise provide too much power to the heating element too rapidly, were it not for the duty cycle. Typically, it is not necessary to use a duty cycle to cool down a heating element, i.e., the power is cut off during the entire cycle, although a duty cycle can be used to regulate or smooth cooling as well. An alternative to using duty cycle control is to use so called chopping.

Another aspect of the invention relates to the detection of the main power supply voltage, e.g., 110V, 240V, etc., and varying the duty cycle in dependence on the detected supply voltage. This is schematically illustrated in FIG. 8, where the main supply voltage is typically 110V or 240V. A switch mode power supply circuit 800 determines the main voltage, e.g., using a variable frequency power supply in which the amplitude of the signal varies with voltage monitored by a peak detector 802. In other embodiments, the voltage can be determined using other techniques, e.g., a fixed frequency switch mode power supply. A signal indicative of the voltage of the main power supply will be sent to the ADC 804. Depending on the detected voltage, the duty cycle can be adjusted, e.g., a lower duty cycle will be selected if the voltage is high (e.g., 240V), and a higher duty cycle will be selected if the voltage is low (e.g., 120V). In variants, the duty cycle may also be varied within a low or high range to regulate the temperature of the heating element. The input voltage is regularly monitored and the duty cycle is varied to compensate for fluctuations in the power supply. In this manner a substantially constant level of power is supplied to the heating element and the heating element is prevented from over heating. This control system provides a substantially consistent humidity level.

The voltage detection system may also be used to detect when the water tub is substantially empty and provide an indication to the user or turn off the humidifier. A substantially empty water tub may be detected by measuring the rate of increase in the temperature of the hot plate. When the tub is substantially empty the temperature will increase rapidly.

In another aspect, the determination of voltage can be used to disable the CPAP device and/or provide a warning to the user. For example, if the peak detector determines that the detected voltage (e.g., 240V), is different than the voltage for which the CPAP device was designed (e.g., 110V), then the microprocessor can disable the CPAP device and/or provide a signal to the user, e.g., "main power supply voltage not suitable for use with this device—see retailer."

Figure 11:
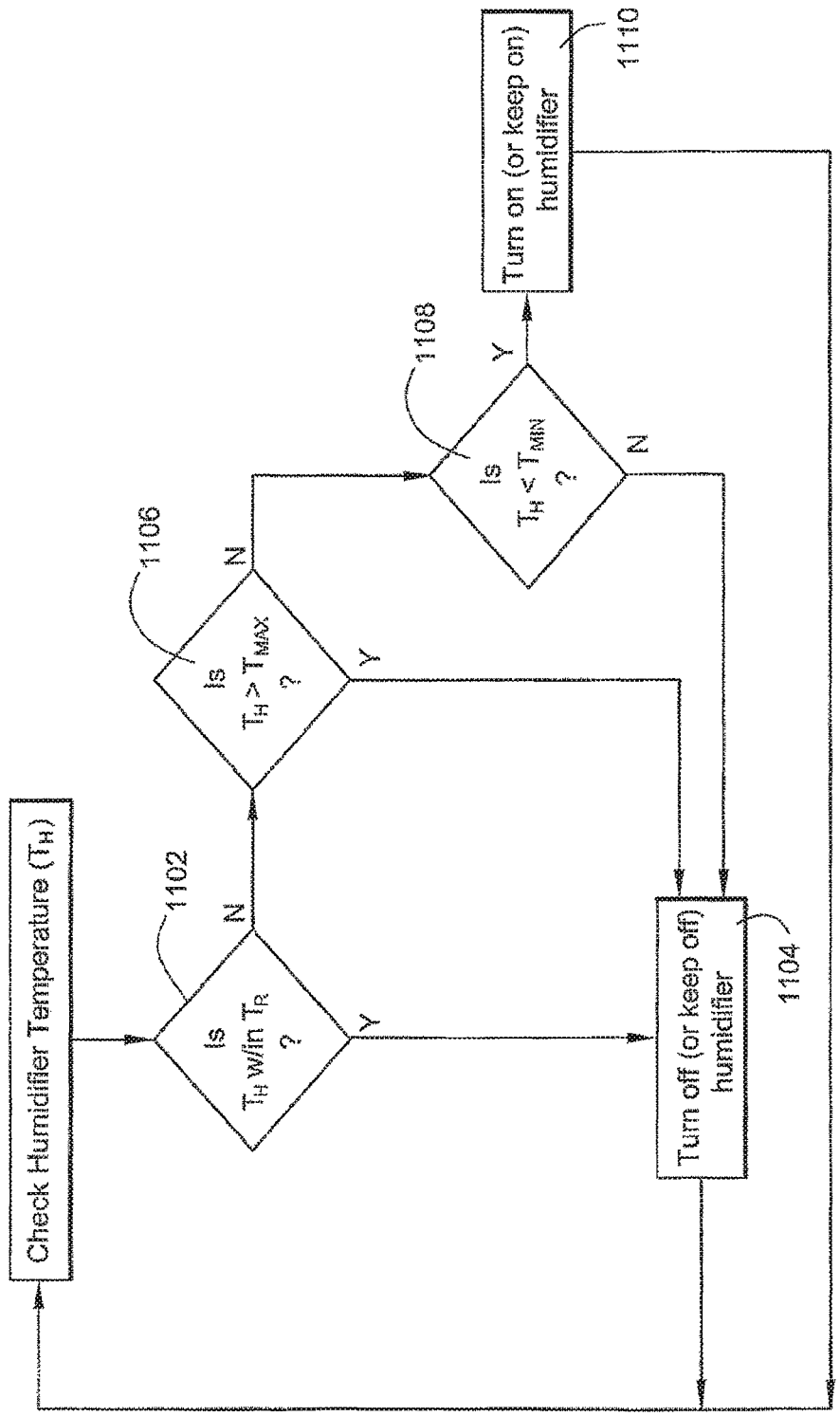

Another algorithm for controlling the temperature of the humidifier is shown in FIG. 11. In step 1102, a determination is made as to whether $T_H$ is within a predetermined temperature target range ($T_R$), which may be 5 or 10 degrees in range. If "yes", a signal is provided to turn off (or keep off) the power to the humidifier heating element (Step 1104). If "no" in step 1102, a determination is made in step 1106 whether $T_H > T_{MAX}$. If "yes", then the power to the humidifier heating element is cut off (Step 1104). If "no", then $T_H$ must be less than $T_{MIN}$ (Step 1108 can be thought of as confirmation that $T_H$ is less than $T_{MIN}$ if steps 1102 and 1106 indicate "no") and a signal is sent to turn on or keep on the power to the humidifier heating element (step 1110). As described above, the duty cycle or slew rate may be employed in which only for a fraction of the cycle time is the power actually supplied to the humidifier heating element. If "no", the program progresses to Step 1104.

In the embodiments of FIGS. 10 and 11, control of the humidifier is carried out using program code which is programmed directly into the flow generator's microprocessor, thereby avoiding the need for an integrated circuit or other hardware in the humidifier. The thermistor 115 in the humidifier may provide its temperature reading in terms of a voltage difference which can be converted by an analog to digital converter (ADC) to a signal which is useable by the microprocessor. When the microprocessor of the flow generator provides a signal to the humidifier to turn the power "on" or "off" to the heating element, the digital signal from the microprocessor may be converted to an analog signal and applied to the humidifier.

Figure 12:
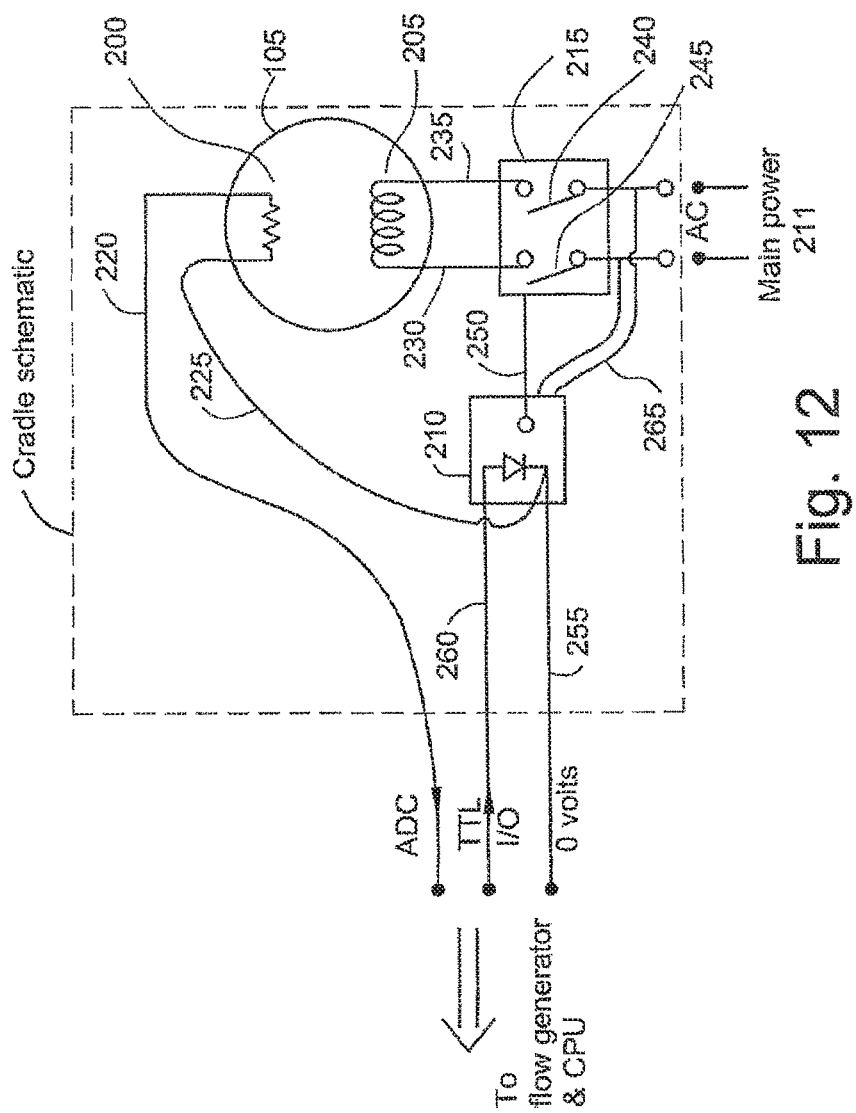
FIG. 12 is a schematic diagram showing one example of electrical components of a cradle according to an embodiment of the present invention.

FIG. 12 is a schematic diagram of the electrical components of a cradle according to an embodiment of the present invention. This can be used in conjunction with the embodiments of FIG. 10 or 11 or other control schemes as well. This schematic has common components compared to the schematic of FIG. 6, but additional electrical components have been schematically illustrated in FIG. 12.

In the example of FIG. 12, the cradle circuit includes a thermistor component 200 and a heating element component 205 which are electrically coupled to a first TRIAC 210 such as an opto-coupled trigger TRIAC and a second preferably low cost TRIAC 215. A TRIAC is a three-terminal semiconductor that controls current in either direction. In general, the first TRIAC 210 provides electrical insulation between the CPU and the main power supply 211. The second TRIAC is a switch for applying current to the heating element 205. In another embodiment, the circuit may include two low cost TRIACs 210, 215.

The thermistor includes two leads 220, 225, one temperature signal lead 220 leads to an ADC which input is provided to the flow generator (CPU). The other lead 225 is provided to the ground (0 volts) connection of the first TRIAC 210. The two leads 230, 235 of the heating element 205 are coupled to the second TRIAC 215, which in this embodiment has two switches 240, 245, each of which is coupled to the AC main power supply 211. The first TRIAC 210 is also coupled to the AC main power supply 211. The first TRIAC controls the switching cycle of the second TRIAC 215 through command line 250.

The first TRIAC 210 includes a ("0" volt) ground 255 and a ITL (I/O) line 260 from the flow generator (CPU). The transistor-transiter-logic (TTL) line conveys switching commands from the microprocessor to the first TRIAC 210. One of the leads (e.g., line 265) from the AC main power supply 211 is configured to supply a signal that detects the zero crossing voltage as the AC power cycles through positive and negative voltages. Zero crossing triggering only allows the TRIAC to switch on or off when the current is zero, thus after a complete AC waveform has occurred. At the zero crossing points, the power is zero and there is no EMC or electrical power noise problem and current surges are eliminated. Accordingly, switching the second TRIAC 215 only at a zero crossing points reduces the risk of power surges and power noise from affecting the electronic circuits in the humidifier and control circuits.

The temperature of the water in the humidifier is determined using a transducer, such as a thermistor 200. The resistance of the thermistor is inversely proportional to the temperature of the thermistor. Thus, at high temperature the thermistor has a low resistance and at low temperatures the thermistor has a high resistance. The resistance of the thermistor determines the voltage applied to the temperature signal lead 220 that is sensed by the ADC of the microprocessor. Accordingly, the voltage signal from the thermistor indicates to the microprocessor the temperature of the water in the humidifier.

The humidifier control program, executed by the microprocessor and shown in FIG. 10 is a more preferred embodiment since it requires less program code and less memory to implement in the microprocessor. However, the humidifier control program embodiment of FIG. 11 may be more power efficient since the temperature need not reach $T_{MAX}$ before the power to the humidifier is cut off. Further, the embodiment of FIG. 11 may be more stable.

4.3.2 Detection of Humidifier Fault Conditions from Temperature Signal

In accordance with an aspect of the invention, the temperature sensor has a gamut of detectable values. Within the gamut are defined a number of ranges including a valid operating range, a low range, and a high range. For example, with reference to FIG. 9, the normal operating range ($T_{MIN}$ to $T_{MAX}$) for a humidifier is about is 5° C. to 70° C. Signals outside the valid operating range are used to infer non-connection of the humidifier or some other error condition, in which case power to the heating element is disconnected.

Figure 13:
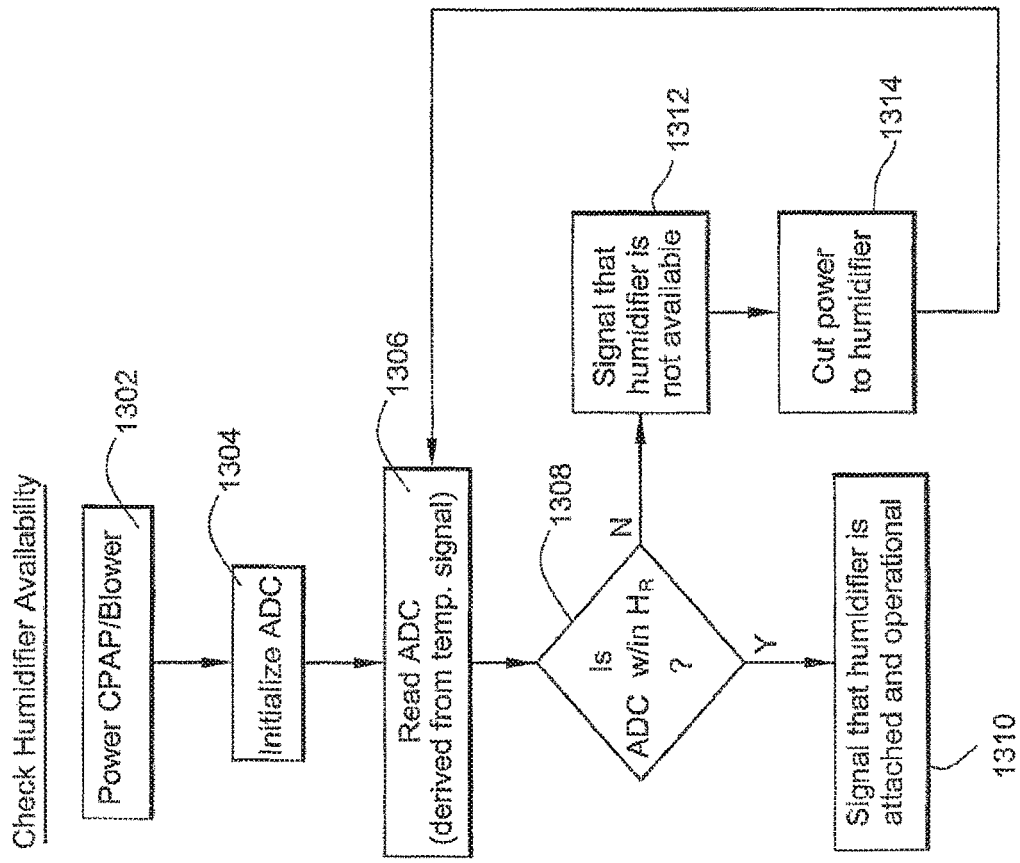
FIG. 13 is a program chart for determining availability of a humidifier or another peripheral component according to an embodiment of the invention.

One aspect of an algorithm is to check the availability (connection and/or operation) of the humidifier as shown in FIG. 13. In Step 1302, power is supplied to the CPAP unit or blower. In Step 1304, the ADC (which is in electrical communication with the humidifier) is initialized. Power is not yet supplied to the heating element 205 of the humidifier. The voltage signal 220 from the humidifier thermistor (an analog signal) is converted by the ADC into a digital value based on the voltage. The analog voltage signal 220 may be converted to one of 255 digital values that are available for an 8-bit digital signal (from an available 10-bit) from the ADC. It is noted that a different number of bits may be used and will consequently generate a different digital value. The digital value outputted by the ADC is indicative of the heater plate temperature in the humidifier, when the humidifier is connected and operating properly to heat water. Them is a normal operating range ($H_R$) of ADC signals that result from normal operation of the humidifier. The ADC signal should be in normal operating range regardless of whether the heating element is on or off. ADC signals out of the normal operating range ($H_R$) may be used by the microprocessor to detect a disconnection of the humidifier or other potential problem.

The digital value is applied to the microprocessor in step 1306. Initially, the microprocessor determines if humidifier is attached and operational by determining whether the digital value from the ADC is within the possible operating range ($H_R$) of the humidifier (Step 1308). The ADC signal will be outside the operating range if the humidifier is not properly electrically connected to the control circuits in the blower/CPAP or the humidifier thermistor is not properly operating. If the microprocessor detects that the ADC signal is within the operating range ($H_R$) of the humidifier, the processor turns on the TTL I/O pin connected to line 260 and generates a humidifier available signal for the LCD to indicate that the humidifier is attached and operational (Step 1310). The humidifier available signal may cause the display, e.g., LCD or LED, on the CPAP device (cradle, flow generator or humidifier), to glow or otherwise show that the humidifier is available and operating. The humidifier available signal can be an audible signal as well.

If the output of the ADC is not within the operating range ($H_R$) of the humidifier, a signal is generated that the humidifier is not available (Step 1312). An ADC output outside the operating range may result from a number of different conditions including but not limited to no humidifier attached, ambient conditions outside working range, humidifier fault. In Step 1314, the power to the humidifier is turned off by commanding (TL 260) the first TRIAC 210 to switch off the second TRIAC 215 that disconnects the heating element from the main power 211, whereupon the humidifier and its connection can be manually checked. The signaling step (1312) may include a "warning" message presented on the display of the CPAP, and this message may be displayed after the power is turned off in step 1314, or steps 1312 and 1314 can be performed simultaneously.

There may also be another branch to this control system that continually detects for valid operation of the humidifier, while the humidifier is heating water for air flowing from the blower. The system detects abnormal conditions such as shorting to ground of the thermistor, humidifier incorrectly plugged in, or the presence of some other device plugged in. Under these circumstances the thermistor analog signal to the ADC will cause the ADC to generate a digital value that is outside the $H_R$. Upon receiving this out-of-$H_R$ range digital value, the microprocessor will determine that a problem has occurred and consequently display a warning message and turn off power to the humidifier 1314. Further, the microprocessor may only determine that a problem has occurred after the out-of-$H_R$ range digital value has persisted for some predetermined period, e.g., one second or one minute periods.

FIG. 13 represents a temperature based control loop to detect whether the humidifier is available. In this example, the thermistor resistance is used as an indicator as to whether the humidifier is connected and/or operational. This can be implemented using software (e.g., with a program as shown in FIG. 13), where the ADC signal is based on the monitoring of thermistor resistance which is typically used to determine the temperature of the water in the humidifier (see Step 1306 in FIG. 13). When the control loop is using the thermistor-ADC signal as an indication of the availability of the humidifier, the microprocessor may read a zero (0) volt reading from the ADC as corresponding to a short circuit in the humidifier and determine that a poor connection or some other error exists in the humidifier. In the converse, if the microprocessor reads the thermistor-ADC signal at five (5) volts (which corresponds to an open circuit—infinite resistance), the processor may interpret this 5-volt signal is indicating either no humidifier present or a poor connection between the humidifier and control circuit. A humidifier detection and control circuit operatively coupled to the flow generator CPU, as shown in FIG. 13.1, can also be provided. This circuit includes a thermistor (or other sensor) within the humidifier that is connected to a voltage divider comprising resistors R32, R41, R47 and R48. A voltage VCC is applied to one end of R32 and an analogue signal $V_{ADC}$, taken from the node between R41 and R48, is input to the ADC (analog-to-digital) portion of the CPU. The CPU outputs a heater high or heater low control signal out of the I/O port depending upon the resistance value of the thermistor. The circuit includes connections to a hardware protection circuit (not shown) which can cause the input to the ADC to go outside of certain limits (either high or low) based upon a fault occurrence, i.e., overheating, short circuit, etc., in the hardware.

$V_{ADC}$ can be used for CPU to 1) read the heater element temperature, 2) detect attachment of a humidifier, 3) check if the attached humidifier is correct and/or 4) check if the attached humidifier has the correct connection. The example Table below calculates $V_{ADC}$ verses thermistor resistance (related to the temperature). FIG. 13.2 is a graph illustrating values that can be utilized by the microprocessor software as an indication of the operation state and/or presence of the humidifier.

| VCC V | $V_{ADC\ V}$ | Rt (K Ohm) | R32 (K Ohm) | R41 (K Ohm) | R47 (K Ohm) | R48 (K Ohm) |
|---|---|---|---|---|---|---|
| 5 | 1.454869359 | 10 | 18 | 27 | 47 | 100 |

4.3.3 Pull-Up Resistor

Figure 15:
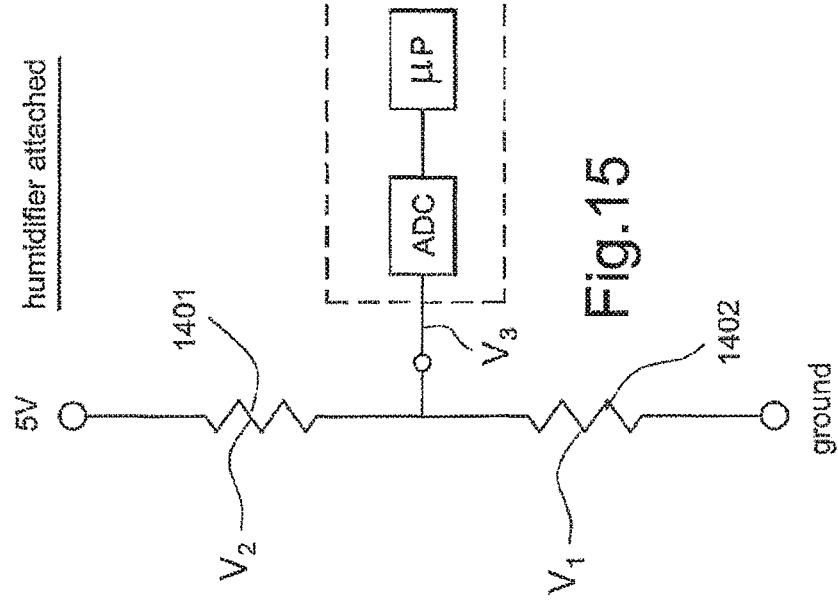
FIGS. 14 and 15 are schematic views of a system for detecting and monitoring a humidifier according to an embodiment of the invention.
Figure 14:
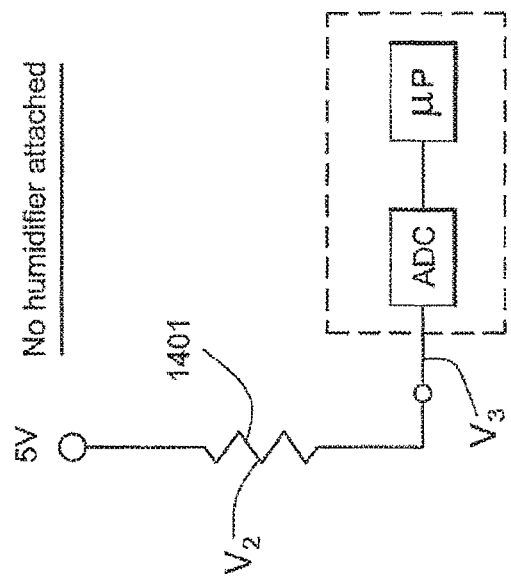

The availability of the humidifier can be detected using a pull-up resistor, as illustrated in FIGS. 14 and 15. The pull-up resistor 1401 may be included in the control circuitry in the blower and may be between a voltage supply, e.g., five volts, and an input to the ADC. In this embodiment, the thermistor 200 is represented by a second resistance 1402 and its voltage signal 220 ($V_1$) is applied to the ADC. The voltage signal ($V_3$) applied to the input of the ADC is converted by the ADC to a digital eight (8) bit signal. If the humidifier is not attached or otherwise is not drawing any power, the humidifier (1402) does not absorb any portion of the voltage and is an open circuit, and thus only the pull-up resistor absorbs voltage and $V_2$ become equal to the $V_3$ voltage applied to the ADC. The microprocessor may determine that a digital signal equivalent to $V_3$ is outside the $H_R$ range and indicates the absence of an operational humidifier. In particular, if the analog voltage ($V_3$) is at the reference voltage level, e.g. 5V or 3.8V, it indicates that there is an open circuit in the thermistor and that the humidifier is not properly attached or not operating properly. In this circumstance, the ADC digital value corresponding to this $V_3$ voltage will be the maximum digital value, e.g., 255. Alternatively, if the thermistor resistance (1402) is zero (short circuit) it will pull $V_3$ to ground (zero volts) and apply a zero level to the ADC, which in turn will output an minimal digital signal, e.g., 1, to the microprocessor. In this case, it is inferred or determined that the humidifier is not available (not attached and/or operating). See FIG. 14.

If the humidifier is connected and operational, the voltage ($V_3$) supplied to the ADC will be less than the reference voltage from the pull-up resistor 1401 and more than zero because of the resistance of the properly connected and operating thermistor 1402.

4.4 Liquid Crystal Display (LCD) Driving

The present system uses an LCD such as a four-digit seven-segment clock (see, e.g., FIGS. 18.1-18.3) as the visual output for the user interface to the CPAP. Typically, an LCD display includes its own LCD driving IC, and all that is required for display is to send data to the LCD driving IC and it will display the data. However, in another embodiment of the present invention, a separate LCD driving IC is eliminated, and the display segments 1802 are driven directly from the TTL data Input/Output (I/O) pins (5 volts) on the flow generator CPU. Preferably, an inexpensive microchip (CPU) is used to drive both the motor and the LCD. An external CPU controls the LCD using multiplexing. To provide external multiplexing is difficult as specific timing and voltage requirements are necessary.

The LCD display is divided into four common domains 1801 (1, 2, 3, 4 in FIGS. 18-1, 19 and 20), e.g., wherein each domain can generate an alphanumeric character. Each common domain is divided into eight character segments 1802, labeled A, B, C, D, E, F and G in FIG. 18-4. Other character segments are periods (DP1, DP2, DP3 in FIG. 18-1) and a colon (COL in FIG. 18-1). The segments for each common domain can together display any one of a selected alphanumeric character. The segments 1802 are switched on and off based on voltages (Va1, Vb1, Vc1 in FIG. 16) applied to the input pins of the LCD display which include common electrode pins (PINs 1 to 4 in FIG. 18-5) and segment electrode input pins (PINs 5 to 12). The four voltages (0V, 1V, 2V and 3V) and the common and segment input pins on the LCD display, to which these voltages may be selectively applied allows for a unique combination of voltages and pins for each alphanumeric character to be displayed. (see FIGS. 16-20). FIG. 18-5 shows the PIN mapping for the electrodes in an LCD display, wherein PINs 1 to 4 correspond to the common electrodes (COM0, . . . COM3) for each of the four common domains 1801, and PINs 5 to 12 correspond to the electrodes for the segments 1802. For example, PIN 5 connects to the segment electrodes for the B, C and G segments of the 4 common domain and for the DP2. Applying a voltage to PIN 5 in combination with a voltage applied to a selected one of the four common PINS 1-4, allows the CPU to drive a selected one of the 4B, 4C, 4G and DP1 segments in the display. The CPU commands for applying the sequences of common and segment voltage levels (0V, 1V, 2V and 3V) to the common and segment electrodes, respectively, of the LCD display is generated by the CPU of the blower. These commands cause the LCD display to show the appropriate alphanumeric characters of the desired message, e.g., "OK" or "OFF".

Each alphanumeric character segment 1802 in an LCD display comprises a top-electrode and a bottom electrode, as shown in FIGS. 18.1-20. This is also schematically illustrated in FIG. 21. In order that the alphanumeric character segment is switched on, there needs to be an appropriate electrical potential between the top and bottom electrodes. In a device in accordance with the present invention, a 3 V potential is recommended. Furthermore, the potential should be alternating each time the segment is switched on. That is, if the top electrode is positive 3 V with respect to the bottom electrode one time, the next time it needs to be negative 3 V with respect to the bottom electrode when it is turned on. Whilst each segment could be individually controlled by a pair of data pins, a more efficient way to control them is to use a system of multiplexing. In this way, fewer data pins are needed to control a given number of segments. Because the electrodes in a display have a capacitance, it is possible to switch them serially, rather than in parallel. The capacitance of the display will cause a segment 1802 to remain at an ON/OFF state for a short period after voltage is switched off to the electrodes for that segment.

Figure 22:
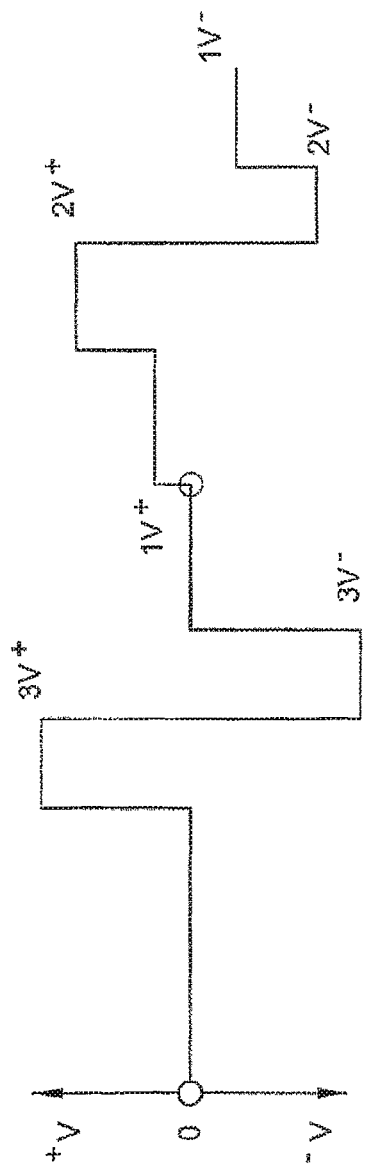
FIG. 22 is a graph explaining exemplary timing aspects of the series-based activation of pixels or other display elements according to an aspect of the present invention.

FIG. 22 shows a voltage cycle for switching the segments in each domain o of a display. Serially switching the LCD data pins provides sufficiently fast switching to provide a character display that is visually perceived to be simultaneously turned on. The maximum refresh time for each segment is 4 milliseconds. Thus the process of displaying information on an LCD display is to follow a complex pattern of applications of alternating 3 V potentials to a the matrix of electrodes of the domains and their segments.

The LCD may have ⅓ biasing, a ¼ duty cycle, and an operating voltage of 3V. As there is a time delay for segment electrodes to reach the appropriate 3 V potential and there is a requirement of quick display responses the system uses biasing (which is $\frac{1}{3}^{rd}$ of the operating voltage). The segments are held at a 1 V bias potential until turned on by applying a 3 V potential. The transition from 1V to 3V is sufficiently fast for display purposes compared to the transition from 0V to 3V. For quick display responses, the display is maintained at 1V, thus requiring a switch between 1V and 3V (as opposed to a switch between 0V and 3V) to cause a display segment 1802 to switch ON/OFF.

The ¼ duty cycle refers to grouping the character segments 1802 into four groups, and only applying full voltage to one group at a time and then moving to the next group. For example, the grouping may be: Group 1—character segments corresponding to common electrode COM0, e.g., 4B, 4A, 3B, 3A, 2B, 2A, 1B and 1A, in the pin array shown in FIG. 18-5; Group 2—character segments corresponding to common electrode COM1; Group 3—character segments corresponding to common electrode COM2, and Group 4—character segments corresponding to common electrode COM3. The common and segment electrodes for each group are powered together for ¼ of the duty cycle. Each group is powered sequentially in the duty cycle. Of course, whether power is supplied to a particular segment also depends on whether the CPU has determined that the segment is to be ON/OFF. Nevertheless, when the CPU has determined that power is to be applied to the common and segment electrodes of a particular electrode, that power is applied only during that ¼ of the power duty cycle for the Group to which the electrode is assigned. In this way each character segment is powered during one-quarter (¼) of the driving time for the duty cycle.

Figure 21:
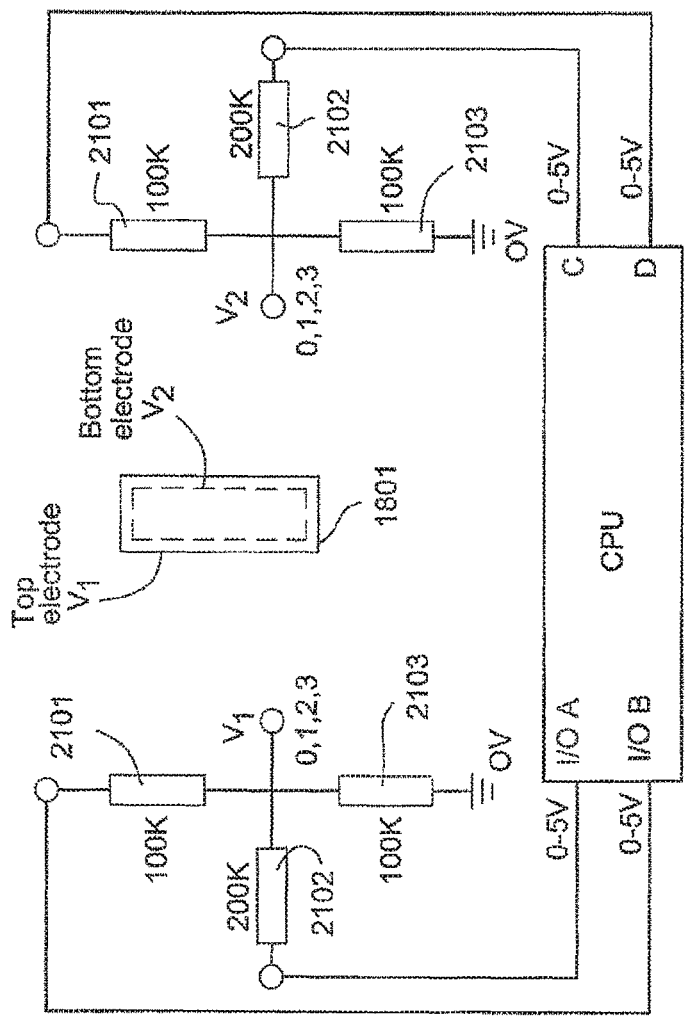
FIG. 21 is a schematic electric diagram showing one possible circuit for driving an LCD according to an aspect of the present invention.

As is shown in FIG. 21, each electrode (common—$V_1$, segment—$V_2$) of a segment 1802 receives a voltage output command from two CPU I/O data pins (I/O A, B or I/O C, D). Thus one segment uses data from four data pins. The TTL logic signal from each pin is either 0 V or 5V. In order to drive an electrode of a character segment with the appropriate combinations of voltages, a pair of pins needs to provide potentials of 0V, 1V, 2V, and 3 V (see FIGS. 17 and 22). Hence an aspect of the invention is a simple and inexpensive circuit that converts two TTL CPU I/O pin outputs into potentials of 0V, 1V, 2V, and 3 V.

Figure 16:
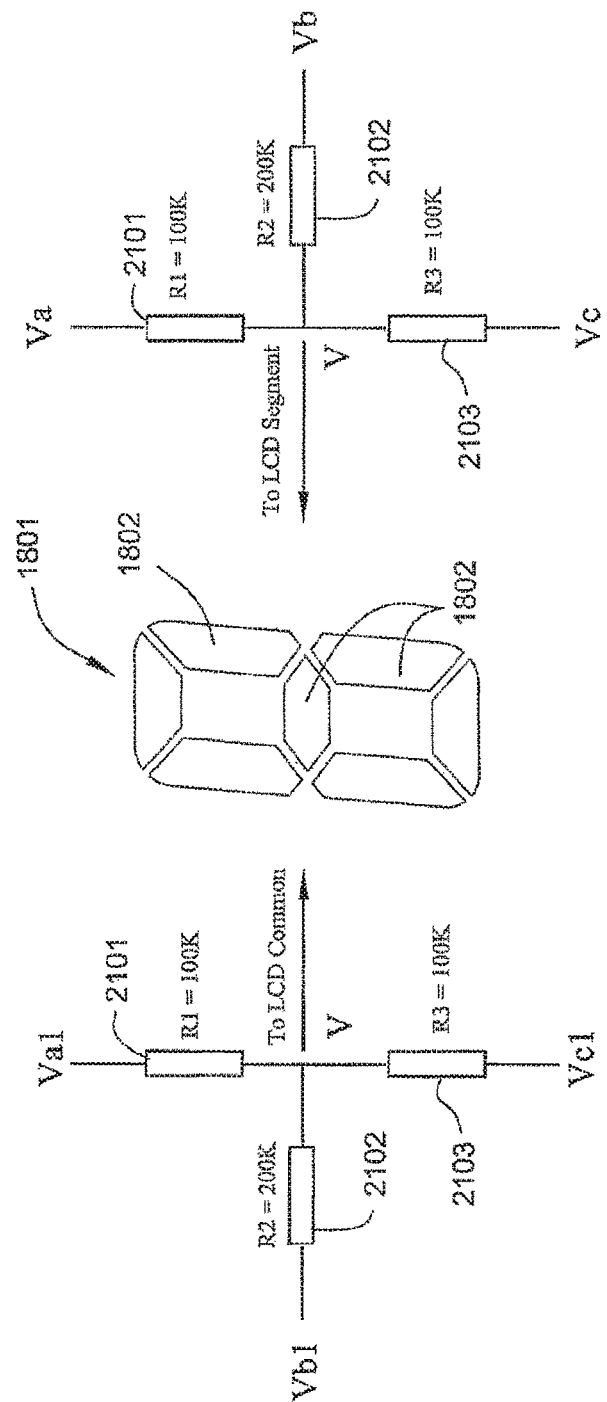
FIG. 16 is a schematic view of a liquid crystal display (LCD) driving circuit according to an embodiment of the present invention.
Figure 19:
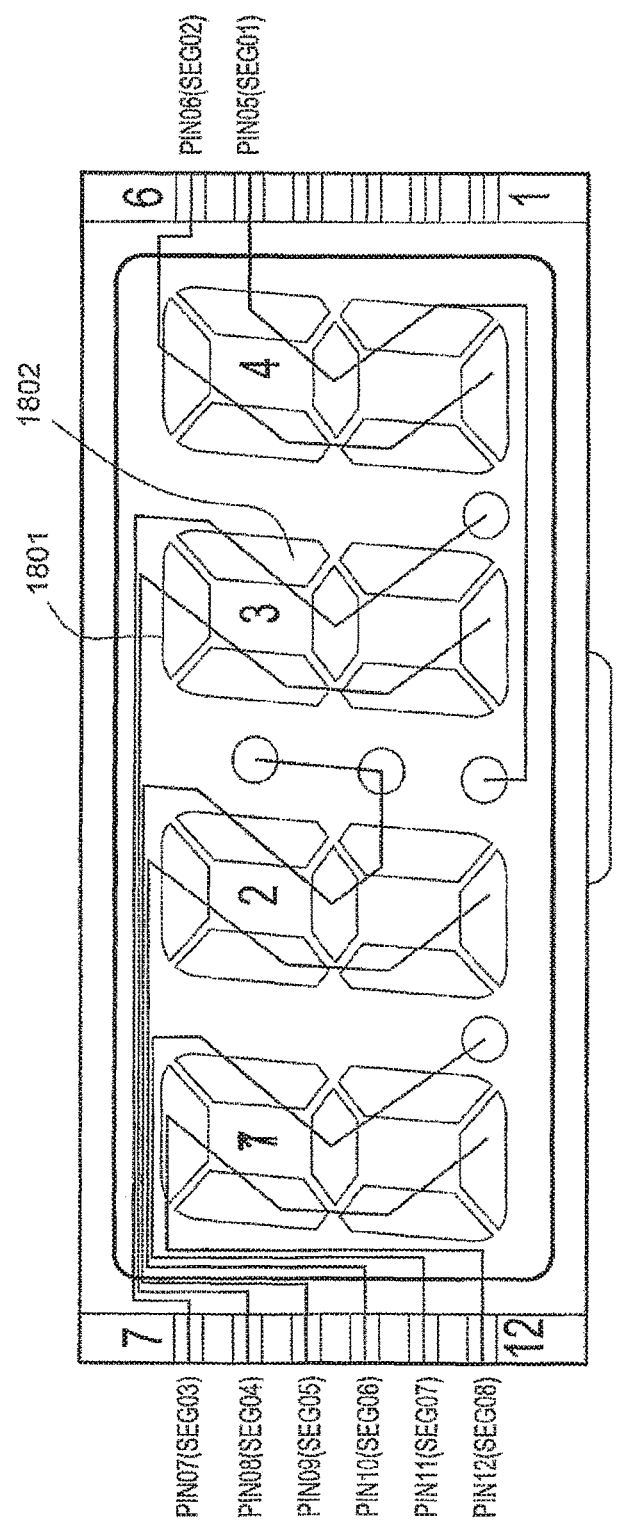
Figure 20:
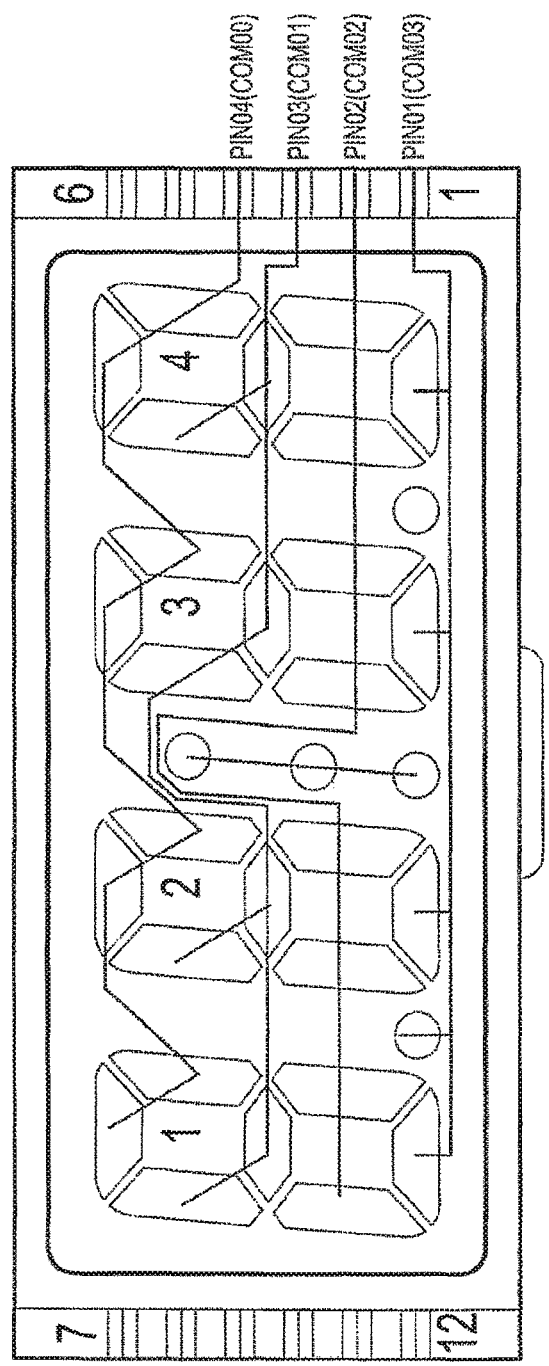

As is shown in the circuit shown in FIG. 21, the voltage levels to be applied to the electrodes of the character segments are achieved by using a combination of three resistors 2101, 2102, 2103, for each electrode. The three resistors may have a resistance ratio of 1:2:1, e.g., 100K, 200K and 100K. Preferably, the resistances are in the range of 50K to 400K. The resistors are arranged as shown in FIG. 16 or 21. Although preferred values of the resistors are indicated above, other values are also possible, e.g., less than 50K and/or greater than 400K. There may be an array of three resistors for each of the input pins [PIN01(COM03), PIN02(COM02) . . . , PIN05(SEG01), . . . PIN12(SEG08)] of the LCD. One of the resistors 2103 is grounded. The other two are connected to a power source at an I/O port of the CPU.

The resistors 2101, 2102 are each connected to a separate TTL I/O port of the CPU. In one embodiment, there may be a pair of CPU I/O ports for each resistor, which would be 48 I/O ports in the case of a 12 pin LCD where each pin has two resistors 2101, 2102 connected to CUP I/O ports. To reduce the number of CPU I/O ports dedicated to driving the LCD, the higher value resistors 2102 can be collectively connected to a common CPU I/O port and each lower value resistor 2101 can be connected to a separate I/O port. In a third embodiment, the lower value resistors 2102 for the common electrode LCD pins (COM00 . . . COM03) are collectively connected to a common CPU I/O port (LCD_C) and, similarly, the lower value resistors 2102 for the segment electrodes (SEG01 . . . . SEG08) are collectively connected to a common CPU I/O port (LCD_S).

4.5 Detection of Motor Fault Conditions

Figure 23:
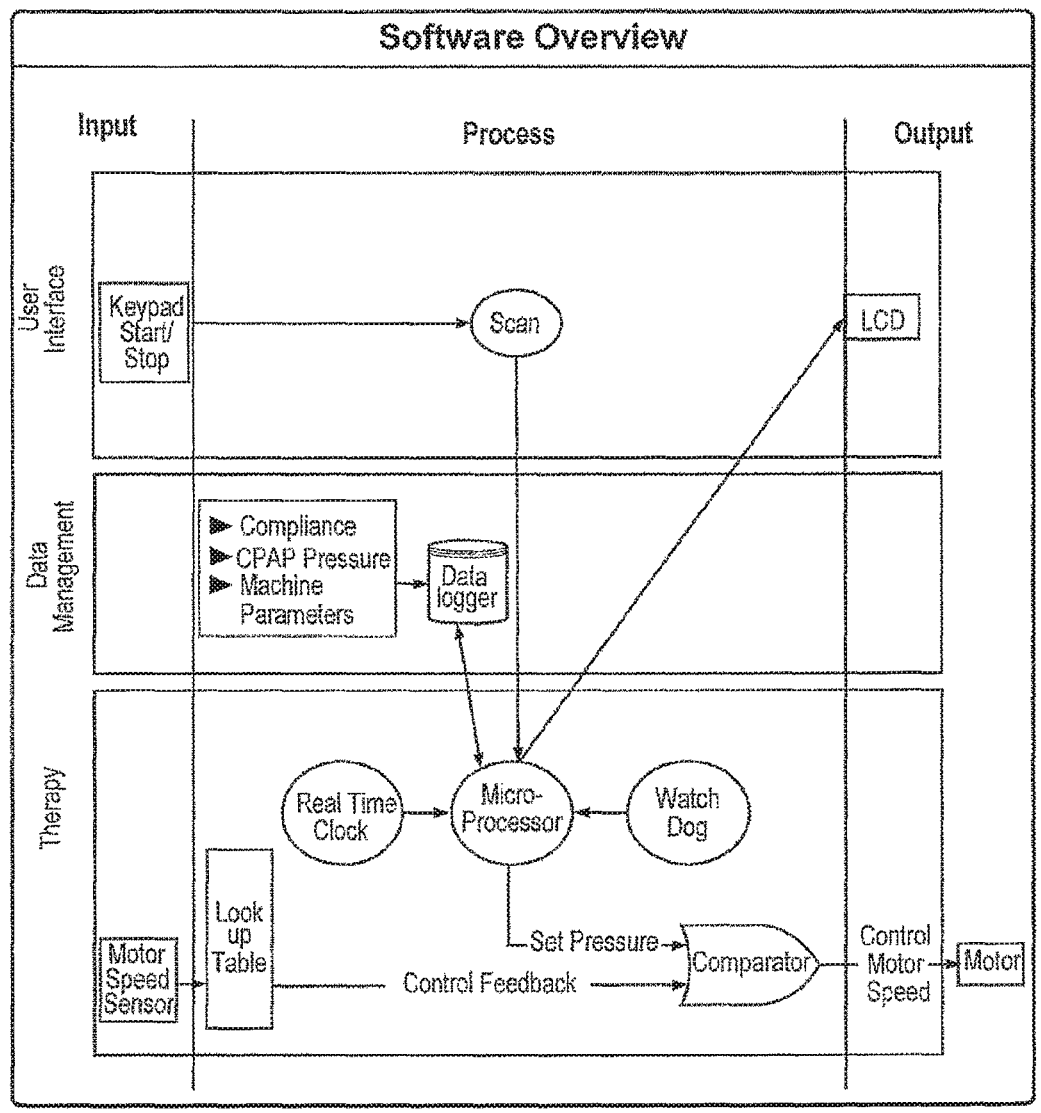
FIG. 23 is a process chart showing a motor speed control circuit according to an embodiment of the present invention.

The microprocessor of the flow generator can also be used to detect fault conditions in the blower motor. FIG. 23 schematically illustrates the general architecture, which includes a User Interface, for example, a keypad, and an LCD. The LCD provides information to the user or clinician such as the total time that the flow generator is ON and set pressure. In conjunction with the keypad and LCD, the patient can set ramp times (as defined within the limits set by the clinician). Embedded software is designed to control the motor speed to produce a pressure as set by the clinician and the software may calculate one or more parameters relating to compliance, e.g., usage hours.

The CPU has a built in motor control functional block that provides the power stage driving signals with PWM control, hall sensor input for commutation control, a software configurable over RPM protection function, and/or motor stall detection function. In addition, the motor RPM may be detected by external hardware and a pull down signal is fed to the CPU as an emergency stop input to stop the motor if the motor RPM exceeds a predefined limit. Software would take appropriate action based on the input, e.g., disable motor, warn patient, vary motor speed, etc. If the motor is running in current mode, the motor current signal can serve as feedback to the CPU motor controller block for real time control. Also the motor current signal (represented by voltage on an ADC input pin) may be provided to the CPU for software to read if system requires detection of semi failing motor.

To gain the best accuracy of motor RPM detection for tolerating the variations on mechanical parameters, working conditions and manufacture tolerances, a full digital motor RPM detection circuit is designed to satisfy the demand. In comparison to the analogue F-V converter approach, one or more of the following advantages can be realized: lower cost; improved accuracy (e.g., no costly timing capacitors that has only 1% tolerance. The accuracy is defined by crystal at PPM level; excellent manufacturability (performance is define by design not manufacture process); multiple suppliers of parts; stable under wide range of operation conditions; configurable to set any required RPM limit.

The flow generator may include a motor speed detection circuit for over RPM protection. As an independent electronic unit (independent of the PCB), the digital circuit provides motor speed detection functions for flow generator control. Also it offers high definition and configurable speed limiting levels.

Figure 24:
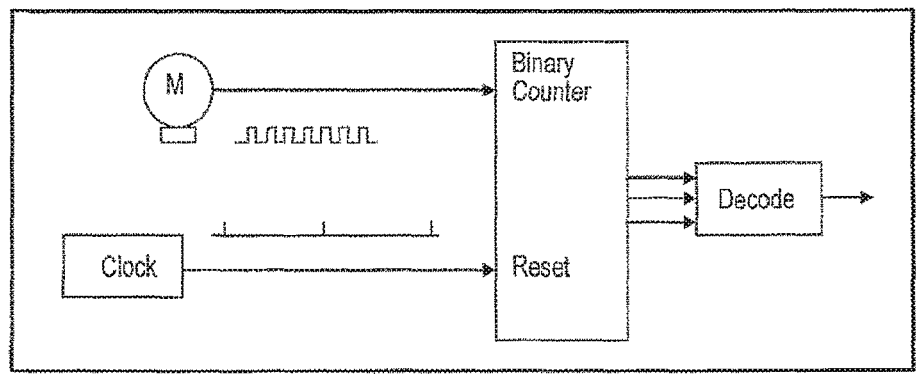
FIG. 24 is a circuit for digital motor speed detection and/or control according an embodiment of the present invention.

An example circuit is shown in FIG. 24. The function of the circuit is to monitor motor sensor output, e.g., from a Hall sensor, optical sensor, etc., accumulate the output (e.g., pulses) over a predetermined amount of time using a clock, and decode these inputs to establish a preset binary code to determine the motor speed level. Generally, the circuit includes three parts: clock timer, counter unit and binary decoder.

In this example, the clock timer uses a 32.768 KHz crystal and *4060IC—a 14 stage binary counter to generate the motor pulse count time base. The 32.768 KHz crystal frequency output, after 14 divisions, establishes a count frequency down to 2 Hz, and this frequency is utilized for the motor speed counting time base.

The counter unit is a resetable multi-stage binary counter, and it counts motor Hall sensor output (pulses) and outputs binary code. The output binary code is increment by each motor pulse as a ripple count, and the count is reset at a fixed time frame (e.g., 2 Hz for this example). The binary decoder is a detector to detect the set binary code. Once the motor pulse counts reach to set binary number within the clock time, it will raise the flag.

The following is an example for calculation of a pre-set binary code. To obtain the binary number for motor speed limit, the maximum pulse rate per each clock cycle is calculated:

Set pulse number=(motor rpm×number of poles/60)/clock frequency

This result (number) is converted into binary code. As a result, each binary digit represents an output of an IC pin Q1, Q2, Q3 . . . Qn.

| As | ... | 1 | 0 | 1 | 1 | 1 | 1 | 1 | 0 | 0 ... |
|---|---|---|---|---|---|---|---|---|---|---|
| | | Q9 | Q8 | Q7 | Q6 | Q5 | Q4 | Q3 | Q2 | Q1 |

By connecting all the 1 digits to the logic AND decoder input, the output '1' is obtained when the output counter meets this code.

This system has the accuracy mainly depending on number of motor pulse per clock time base. For the clock it is based on 32.768 KHz crystal at +/−100 ppm−10 to 70° C. For example, if clock time base is set to 0.5 s, the tolerance=0.5×0.0001=+0.00005 s. The clock tolerance is much greater than motor pulse frequency (0.0013 s at 28 Krpm) so it can only cause ±1 motor pulse error, (for 4 poles motor it has 2 pulses per turn therefore only ±0.5 turns per clock time base).

Total accuracy =

$$\frac{\text{motor pulsing time per clock time base} \pm 1 \text{ pulse time}}{\text{clock time base}}$$

This formula is true only when motor speed is at the set speed point. If motor speed is over the speed limits, it will trip out when the motor's pulse count reaches the set value before the clock resets the counter. The motor speed sensor can be associated with a look up table, as shown in FIG. 23.

In addition or in the alternative, a temperature monitor may be provided, e.g., in the flow generator. For example, a thermistor may be mounted on the flow generator PCB near the CPU that is on top of motor housing that provide the monitoring signal for CPU to identify the over temperature condition on main PCB directly and the motor indirectly. The temperature signal is converted to a voltage for CPU to read using an ADC channel.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. For example in an alternative embodiment the humidifier may be detected using a pull-down resistor instead of a pull-up resistor.

Also, the various embodiments described above may be implemented in conjunction with other embodiments, e.g., aspects of one embodiment may be combined with aspects of another embodiment to realize yet other embodiments. Further, each component or feature of each embodiment alone may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

The invention claimed is:

1. A method for controlling a Continuous Positive Airway Pressure (CPAP) device comprising a blower configured to provide a supply of breathable gas, a humidifier including a heating element, and a switch selectively operable to connect and disconnect the heating element to a main power supply, the method comprising:
   supplying a main power to the CPAP device from the main power supply;
   monitoring a voltage of the main power;
   comparing the monitored voltage to a predetermined voltage; and
   adjusting a duty cycle of the heating element based on the comparison of the monitored voltage to the predetermined voltage, wherein the duty cycle of the heating element is adjusted by controlling the operation of the switch when the monitored voltage does not equal the predetermined voltage.

2. The method of claim 1, wherein the method further comprising:
   providing by the blower of the CPAP device a supply of breathable gas in a range of 4 cmH$_2$O to 20 cmH$_2$O;
   powering the heating element to heat water in the humidifier; and
   providing moisture from the heated water in the humidifier to the supply of breathable gas.

3. The method of claim 1, wherein the adjusting the duty cycle includes:
   operating the heating element at a first duty cycle value, and
   selecting a second duty cycle value lower than the first duty cycle value when the monitored voltage is higher than the predetermined voltage.

4. The method of claim 1, wherein the adjusting the duty cycle includes:
   operating the heating element at a first duty cycle value, and
   selecting a second duty cycle value higher than the first duty cycle value when the monitored voltage is lower than the predetermined voltage.

5. The method of claim 1, wherein the adjusting the duty cycle includes:
   operating the heating element at a first duty cycle value,
   operating the heating element at a second duty cycle value lower than the first duty cycle value, and
   operating the heating element at a third duty cycle value higher than the first duty cycle value.

6. The method of claim 1, wherein:
   the supplying the main power to the CPAP device includes powering the heating element based on a first value of the duty cycle, and
   the adjusting the duty cycle includes varying the duty cycle within a range lower than the first value of the duty cycle to regulate a temperature of the heating element.

7. The method of claim 1, wherein:
   the supplying the main power to the CPAP device includes powering the heating element based on a first value of the duty cycle, and the adjusting the duty cycle includes varying the duty cycle within a range higher than the first value of the duty cycle to regulate a temperature of the heating element.

8. The method of claim 1, wherein the adjusting the duty cycle includes varying the duty cycle within a range from 1 percent to 100 percent.

9. The method of claim 1, further comprising:
disabling the CPAP device when the monitored voltage is not equal to the predetermined voltage; and
providing a warning signal via the CPAP device.

10. The method of claim 1, wherein the adjusting the duty cycle includes supplying a substantially constant power level to the heating element by varying the duty cycle to compensate for fluctuations in the power supply.

11. The method of claim 1, wherein the adjusting the duty cycle further includes preventing the heating element from overheating by varying the duty cycle to compensate for fluctuations in the power supply.

12. A method for controlling a Continuous Positive Airway Pressure (CPAP) device, the method comprising:
supplying a main power to the CPAP device;
monitoring a voltage of the main power;
comparing the monitored voltage to a predetermined voltage; and
adjusting a duty cycle of a component of the CPAP device based on the comparison of the monitored voltage to the predetermined voltage, wherein the monitoring a voltage of the main power is by an analog circuit having an output connected to an input of an analog-to-digital converter, the analog-to-digital converter having an output,
the comparing the monitored voltage to a predetermined voltage is by a controller having an input connected to receive from the output of the analog-to-digital converter a signal corresponding to the monitored voltage, and
the adjusting the duty cycle is according to a program executed by the controller, the controller having an output connected to a switch operable to open and close a circuit between the main power and the component.

13. A method for controlling a Continuous Positive Airway Pressure (CPAP) device comprising a blower and a humidifier including a heating element, the method comprising:
supplying a main power to the CPAP device;
monitoring a voltage of the main power;
comparing the monitored voltage to a predetermined voltage;
adjusting a duty cycle of the heating element based on the comparison of the monitored voltage to the predetermined voltage;
determining a predicted rate of temperature increase in the heating element; and
determining that a water tub of the CPAP device is substantially empty based on the predicted rate of temperature increase in the heating element.

14. A Continuous Positive Airway Pressure (CPAP) device comprising:
a blower configured to provide a supply of breathable gas;
a humidifier including a heating element;
a switch selectively operable to connect and disconnect the heating element to a main power supply;
a voltage detection system configured to monitor a voltage of the main power supply; and
a controller configured to
receive from the voltage detection system a value corresponding to the monitored voltage,
compare the value of the monitored voltage to a predetermined value, and
adjust a duty cycle of the heating element by controlling an operation of the switch when the value of the monitored voltage does not equal the predetermined value.

15. The CPAP device according to claim 14, wherein the blower is configured to provide the supply of breathable gas in a range of 4 cmH$_2$O to 20 cmH$_2$O; and
the humidifier is configured to humidify the supply of breathable gas, wherein the heating element is configured to be in thermal contact with a body of water in the humidifier.

16. The CPAP device according to claim 14, wherein the controller is further configured to provide a substantially consistent humidity level by adjusting the duty cycle such that a substantially constant level of power is provided to the heating element.

17. The CPAP device according to claim 14, wherein the controller is further configured to adjust the duty cycle to prevent the heating element from overheating.

18. A Continuous Positive Airway Pressure (CPAP) device comprising:
a switch selectively operable to connect and disconnect a component to a main power supply;
a voltage detection system configured to monitor a voltage of the main power supply, the voltage detection system including a switch mode power supply circuit and a peak detector and
a controller configured to
receive from the voltage detection system a value corresponding to the monitored voltage,
compare the value of the monitored voltage to a predetermined value, and
adjust a duty cycle of the component by controlling an operation of the switch when the value of the monitored voltage does not equal the predetermined value.

19. A Continuous Positive Airway Pressure (CPAP) device comprising:
a switch selectively operable to connect and disconnect a component to a main power supply;
a voltage detection system configured to monitor a voltage of the main power supply, the voltage detection system including a fixed frequency switch mode power supply; and
a controller configured to
receive from the voltage detection system a value corresponding to the monitored voltage,
compare the value of the monitored voltage to a predetermined value, and
adjust a duty cycle of the component by controlling an operation of the switch when the value of the monitored voltage does not equal the predetermined value.

20. The CPAP device according to claim 14, further comprising:
a water tub in thermal contact with the heating element; and
a temperature sensor configured to measure a temperature of water in the water tub, wherein the controller is further configured to
determine a predicted rate of temperature increase based on the duty cycle and a frequency of the duty cycle, determine a measured rate of temperature increase based on an output from the temperature sensor, and determine that the water tub is substantially empty based on the measured rate exceeding the predicted rate.

* * * * *